US012784871B2

(12) United States Patent
Coogan

(10) Patent No.: US 12,784,871 B2
(45) Date of Patent: Nov. 3, 2026

(54) TOOL FOR ASSESSING AND CALCULATING BIODIVERSITY

(71) Applicant: TTU Holdings Limited, Wellington (GB)

(72) Inventor: Lance Reginald Charles Coogan, Kent (GB)

(73) Assignee: TTU Holdings Limited, Wellington (GB)

( * ) Notice: Subject to any disclaimer, the term of this patent is extended or adjusted under 35 U.S.C. 154(b) by 863 days.

(21) Appl. No.: 18/138,365

(22) Filed: Apr. 24, 2023

(65) Prior Publication Data

US 2024/0355409 A1 Oct. 24, 2024

(51) Int. Cl.
*G16B 10/00* (2019.01)
*G16B 50/00* (2019.01)

(52) U.S. Cl.
CPC ............. *G16B 10/00* (2019.02); *G16B 50/00* (2019.02)

(58) Field of Classification Search
None
See application file for complete search history.

(56) References Cited

U.S. PATENT DOCUMENTS 11,842,537 B1 * 12/2023 Jain ...................... G06V 10/764

OTHER PUBLICATIONS

Yu, Dong Su, et al., "VBioindex: A Visual Tool to Estimate Biodiversity", Genomics & Informatics, vol. 13, No. 3, (2015), 3 pgs.

* cited by examiner

*Primary Examiner* — Michael Fuelling
(74) *Attorney, Agent, or Firm* — Schwegman Lundberg & Woessner, P.A.

(57) ABSTRACT

Example methods and systems are directed to an automated tool for generating a biodiversity indicator. A graphical user interface (GUI) is presented at a user device. First data is received via the GUI. The first data identifies a plurality of species associated with a geographic region. Second data is accessed that comprises, for each species, a reference value and a current value of each of a plurality of biodiversity metrics. The biodiversity indicator for the geographic region is generated based on the second data. A graphical element that includes the biodiversity indicator is automatically generated and presented at the user device.

20 Claims, 10 Drawing Sheets

TOOL FOR ASSESSING AND CALCULATING BIODIVERSITY

TECHNICAL FIELD

Subject matter disclosed herein relates to computerized arrangements for assessing biodiversity in geographic regions. More specifically (but not exclusively), the subject matter relates to the generation of biodiversity indicators. The subject matter disclosed herein further relates to graphical user interfaces suitable for use in generating, presenting, or adjusting such biodiversity indicators.

BACKGROUND

Biological diversity, also known as biodiversity, is an important concept, both due to the inherent value of biodiversity in nature and the benefits that flow from maintaining or improving the biodiversity in a geographic region. Biodiversity can be measured using traditional metrics, such as species richness, species evenness, or relative dominance, or using traditional indices, such as the Shannon-Wiener Index or Simpson's Diversity Index.

BRIEF DESCRIPTION OF THE DRAWINGS

Some embodiments are illustrated by way of example and not limitation in the figures of the accompanying drawings. In the drawings, which are not necessarily drawn to scale, like numerals may describe similar components in different views. To easily identify the discussion of any particular element or act, the most significant digit or digits in a reference number refer to the figure number in which that element is first introduced. Some non-limiting examples are illustrated in the figures of the accompanying drawings in which.

DETAILED DESCRIPTION

Figure 1:
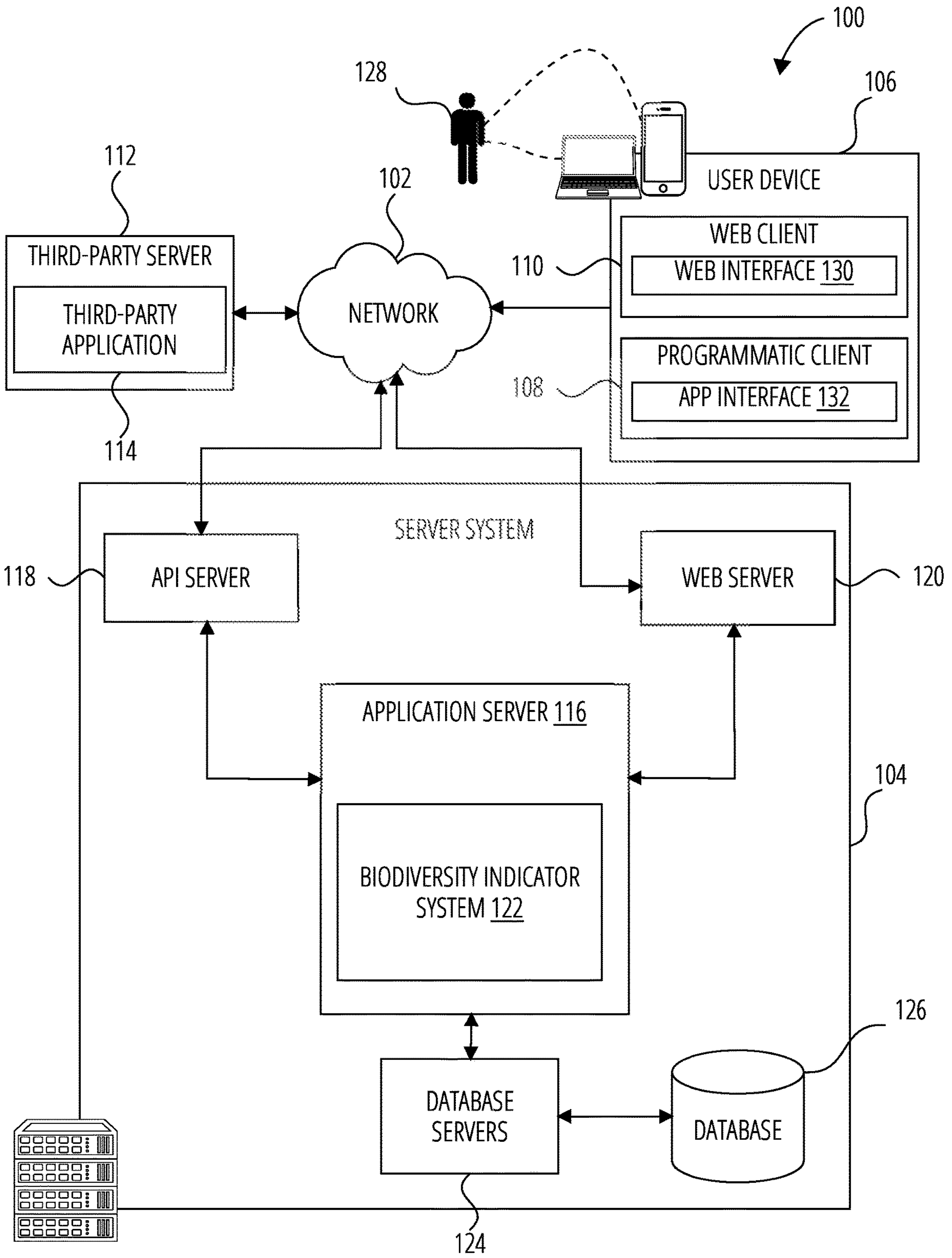
FIG. 1 is a diagrammatic representation of a network environment suitable for automatic generation of biodiversity indicators, according to some examples.

Example methods and systems address the generation of biodiversity indicators, in accordance with examples, for geographic regions. A biodiversity indicator, also referred to as a biodiversity index, may provide a numerical representation of biodiversity in a geographic region, and may be a useful tool in assessing the biodiversity in the geographic region. The geographic region may range from a relatively large region (e.g., a country or large natural park) to a relatively small region (e.g., a farm or residential estate, or property earmarked for development), and may cover one or more different types of natural environments or geographic features, such as land, ocean, mountains, lakes, and rivers (or other freshwater environments).

A biodiversity indicator may be automatically generated based on values associated with a listing of species. The species may include animals (e.g., elephant, lion, buffalo, or springbuck) and plants (e.g., camel thorn, sickle bush, camphor bush, or velvet raisin). The values may include reference values (e.g., baseline values relating to a defined historical date) and current values (e.g., "present day" values) for specified biodiversity metrics.

In some examples of the present disclosure, a graphical user interface (GUI) is presented at a user device. Input data is received via the GUI, e.g., from a user device of a user. The input data may identify a plurality of species associated with a geographic region. The input data may further include, for each species, values of one or more biodiversity metrics. Examples of the present disclosure provide for both a reference value (e.g., a historic value) and a current value of a biodiversity metric to be analyzed.

A biodiversity indicator system, in accordance with some examples, may generate a biodiversity indicator for the geographic region based on the input data. In some examples, the biodiversity indicator is converted from a non-standardized format to a standardized format, e.g., by expressing a current biodiversity index score as a percentage of a reference biodiversity index score. A biodiversity indicator generated by the system for a selected geographic region may provide an indication of a "present day scenario," e.g., representing fauna and flora as they currently exist within the geographic region, while a reference indicator provides an indication of "what it once was," or historical condition. For example, the historical condition may refer to the fauna and flora that existed within the geographic region prior to destructive interference by humankind, or prior to climate changes. In some examples, the system may analyze reference values for a plurality of historic dates, e.g., to track changes in biodiversity across a time series.

Example systems and methods are capable of accounting for complex factors, such as organism type, migration, and invasive species. In some examples, the biodiversity indicator system detects that a particular species is categorized as invasive or migratory (e.g., in a particular context, domestic cats may be categorized as invasive, and elephants may be categorized as migratory), and automatically applies a penalty (or any other weighting factor) or otherwise causes an automatic adjustment (e.g., reduction) in the value of the biodiversity indicator.

The biodiversity indicator system may generate a primary biodiversity indicator and a plurality of supplementary biodiversity indicators. For example, the primary biodiversity indicator may provide a numerical representation of overall biodiversity in the geographic region (e.g., compared to "what it once was," or compared to a specific reference date, as mentioned above), while a supplementary biodiversity indicator covers a specific aspect of biodiversity, such as species richness or concentration in the geographic region.

In some examples, a primary biodiversity indicator or a supplementary biodiversity indicator may be associated with, or expressed as, a monetary value. For example, biodiversity index scores may be associated with monetary values by considering monetary values of animals and plants in a specific geographic region. The biodiversity indicator system may output a current score and a reference score as monetary values, thereby to enable a user to assess, for example, the current monetary value of biodiversity within the specific geographic region against a historic monetary value for the same region.

In some examples, the GUI provides visual distinctions between different categories of species, such as fauna, flora, land, air, water, ocean, migratory, or invasive species (or combinations thereof). Graphical elements indicative of biodiversity indicators may be automatically generated and presented to the user via the GUI. The biodiversity indicator system may visually distinguish between certain graphical elements, e.g., between a primary biodiversity indicator and a reference indicator.

Examples of the present disclosure provide a tool that is user-friendly and highly automated, but still takes complex biodiversity factors (e.g., bio-dominance, scarcity, migration, and invasive species) into account. The tool according to examples of the present disclosure may provide a biodiversity indicator, or multiple indicators, that are meaningful and broadly applicable. Further, user interfaces are provided that allow users to obtain these indicators in an intuitive and efficient manner (e.g., through simplified inputs and visual distinctions between indicator elements).

When the effects in this disclosure are considered in aggregate, one or more of the methodologies described herein may obviate a need for certain efforts or resources that otherwise would be involved in data extraction. Computing resources used by one or more machines (e.g., a personal computer, a tablet, or a server), databases, or networks may be more efficiently utilized or even reduced, e.g., as a result of automatic scoring or prediction generation, user interface design or arrangements, or reduced manual inputs or selections required. Examples of such computing resources may include processor cycles, network traffic, memory usage, graphics processing unit (GPU) resources, data storage capacity, power consumption, and cooling capacity. Various examples described herein can be deployed on a standalone computing device (e.g., a portable computing device such as a mobile phone, laptop, or tablet computer), or in a distributed environment (e.g., an Internet-based client-server environment).

FIG. 1 is a diagrammatic representation of a networked computing environment 100 in which some examples of the present disclosure may be implemented or deployed. One or more servers in a server system 104 provide server-side functionality via a network 102 to a networked device, in the example form of a user device 106 that is accessed by a user 128. A web client 110 (e.g., a browser) or a programmatic client 108 (e.g., an "app") may be hosted and executed on the user device 106.

An Application Program Interface (API) server 118 and a web server 120 provide respective programmatic and web interfaces to components of the server system 104. A specific application server 116 hosts a biodiversity indicator system 122, which includes components, modules, or applications.

The user device 106 can communicate with the application server 116, e.g., via the web interface supported by the web server 120 or via the programmatic interface provided by the API server 118. It will be appreciated that, although only a single user device 106 is shown in FIG. 1, a plurality of user devices may be communicatively coupled to the server system 104 in some examples. Further, while certain functions (e.g., functions of the biodiversity indicator system 122) are described herein as being performed at either the user device 106 (e.g., web client 110 or programmatic client 108) or the server system 104, the location of certain functionality either within the user device 106 or the server system 104 may be a design choice. In some examples, particular technology and functionality may be deployed within the server system 104. In other examples, such technology and functionality may be deployed within a programmatic client.

The application server 116 is communicatively coupled to database servers 124, facilitating access to an information storage repository or database 126. In some examples, the database 126 includes storage devices that store information to be processed or transmitted by the biodiversity indicator system 122.

The application server 116 accesses application data (e.g., application data stored by the database servers 124) to provide one or more applications to the user device 106 via a web interface 130 or an app interface 132. For example, and as described further below according to examples, and with reference to FIGS. 2-8, the application server 116, using the biodiversity indicator system 122, may provide a biodiversity indicator application. The user 128 may access the biodiversity indicator application using a dedicated programmatic client 108 (e.g., installed on a computing device, such as a desktop computer or a portable computing device), with some functionality being provided client-side and other functionality provided server-side. Some or all functionality of the biodiversity indicator application may thus be deployed by a programmatic client 108 executing on the user device 106.

The biodiversity indicator application may provide a GUI via the app interface 132 or the web interface 130 that enables the user 128 to provide input data and view or receive outputs generated by the biodiversity indicator system 122. To access the biodiversity indicator application provided by the biodiversity indicator system 122, the user 128 may create an account with an entity associated with the server system 104, e.g., a service provider (or access an existing account with the entity). The user 128 may use account credentials to access the app interface 132 or web interface 130 (via a suitable web browser) and request access to the biodiversity indicator application. In some examples, the biodiversity indicator system 122 may automatically create a service instance associated with the biodiversity indicator application at the application server 116 which can be accessed by the user device 106 via one or more service APIs to utilize functionality described herein.

One or more of the application server 116, the database servers 124, the API server 118, and the web server 120, may each be implemented in a computer system (e.g., a personal computer, a tablet computer, or a mobile phone), in whole or in part, as described below with respect to FIG. 10. In some examples, third-party applications, such as a third-party application 114 executing on a third-party server 112, can communicate with the application server 116 via the programmatic interface provided by the API server 118. For example, a third-party application may support one or more features or functions on a website or platform hosted by a third party, or may perform methodologies described herein and provide input or output information to the application server 116 for further processing or publication. For example, the third-party application 114 may provide values of certain biodiversity metrics (e.g., scarcity values for certain species) to the biodiversity indicator system 122 for downstream use.

The network 102 may be any network that enables communication between or among machines, databases, and devices. Accordingly, the network 102 may be a wired network, a wireless network (e.g., a mobile or cellular network), or any suitable combination thereof. The network 102 may include one or more portions that constitute a private network, a public network (e.g., the Internet), or any suitable combination thereof. The network 102 may be employed to provide the user 128 of the user device 106 with remote access to the GUI of the biodiversity indicator application to enable the user 128 to input certain data, e.g., to update, via the user device 106, the current values of biodiversity metrics, thereby to cause automatic updating of one or more biodiversity indicators within the GUI.

Figure 2:
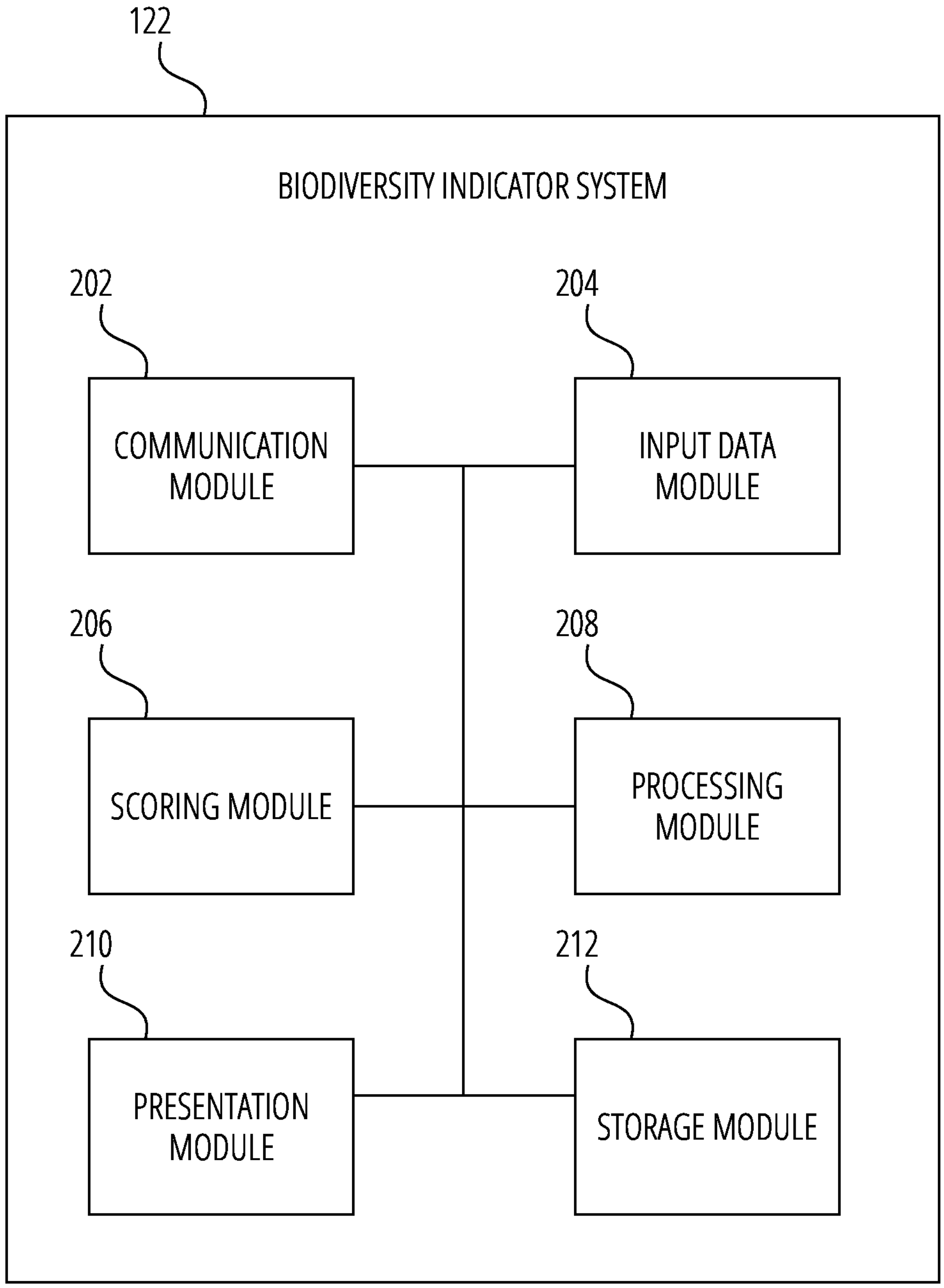
FIG. 2 is a block diagram of components of a biodiversity indicator system, according to some examples.

FIG. 2 is a block diagram of a biodiversity indicator system 122, suitable for automatic generation and presentation of biodiversity indicators, according to some examples. The biodiversity indicator system 122 is shown by way of examples as including a communication module 202, an input data module 204, a scoring module 206, a processing module 208, a presentation module 210, and a storage module 212. At least some of the modules shown in FIG. 2 are configured to communicate with each other (e.g., via a bus, shared memory, or a switch) to implement aspects of the biodiversity indicator application. Any one or more of the modules described herein may be implemented using hardware (e.g., a processor of a machine). For example, any module described herein may be implemented by a hardware processor configured to perform the operations described herein for that module. Moreover, any two or more of these modules may be combined into a single module, and the functions described herein for a single module may be subdivided among multiple modules. Furthermore, according to various examples, modules described herein as being implemented within a single machine, database, or device may be distributed across multiple machines, databases, or devices, or provided on a standalone device.

The communication module 202 receives data sent to the biodiversity indicator system 122 and transmits data from the biodiversity indicator system 122. For example, the communication module 202 may receive, from the third-party server 112, values (or other data) of biodiversity metrics for processing by the other components of the biodiversity indicator system 122 (e.g., abundance data, bio-dominance data, migration data, or scarcity data). Further, the communication module 202 may receive user input, such as biodiversity metric values (or other data), species listings (e.g., a list of animals and plants found in a specific region), or geographic region data, via the user device 106. In some examples, the communication module 202 may receive from the user device 106, or access from some other component, monetary values associated with relevant species (e.g., historic and current prices).

In some examples, reference values (e.g., baseline or historical data relating to species in a particular region) are pre-populated within the biodiversity indicator application, or automatically populated by the biodiversity indicator application once species have been input or selected. Further, current values (e.g., data as observed through counting or obtained using other methods) may be input by a user or retrieved from a database and related to the reference values.

The input data module 204 is responsible for managing input data relating to species, categories, and biodiversity metrics for one or more geographic regions. For example, the input data module 204 may relate and store species data and biodiversity metric values in the database 126, e.g., according to species categories. The scoring module 206 is configured to generate various biodiversity index-related scores, based on the input data. These scores may include, for example, reference weighting coefficients, current weighting coefficients, reference index values, current index values, as described further below.

The processing module 208 is responsible for processing input data and scores generated by the input data module 204 or the scoring module 206, and to generate one or more biodiversity indicators for a particular geographic region. The processing module 208 may also automatically update indicators in response adjustments made, e.g., by the user 128. Output data may be transmitted to the user device 106 by the communication module 202 or presented on a GUI, e.g., the app interface 132, by the presentation module 210. Examples of such a GUI are discussed below, with reference to FIGS. 4-8. Communications sent and received by the communication module 202 may be intermediated by the network 102, while the storage module 212 may enable or facilitate storage of input data, processed data, or output data, e.g., in the database 126 or locally at the user device 106.

Figure 3:
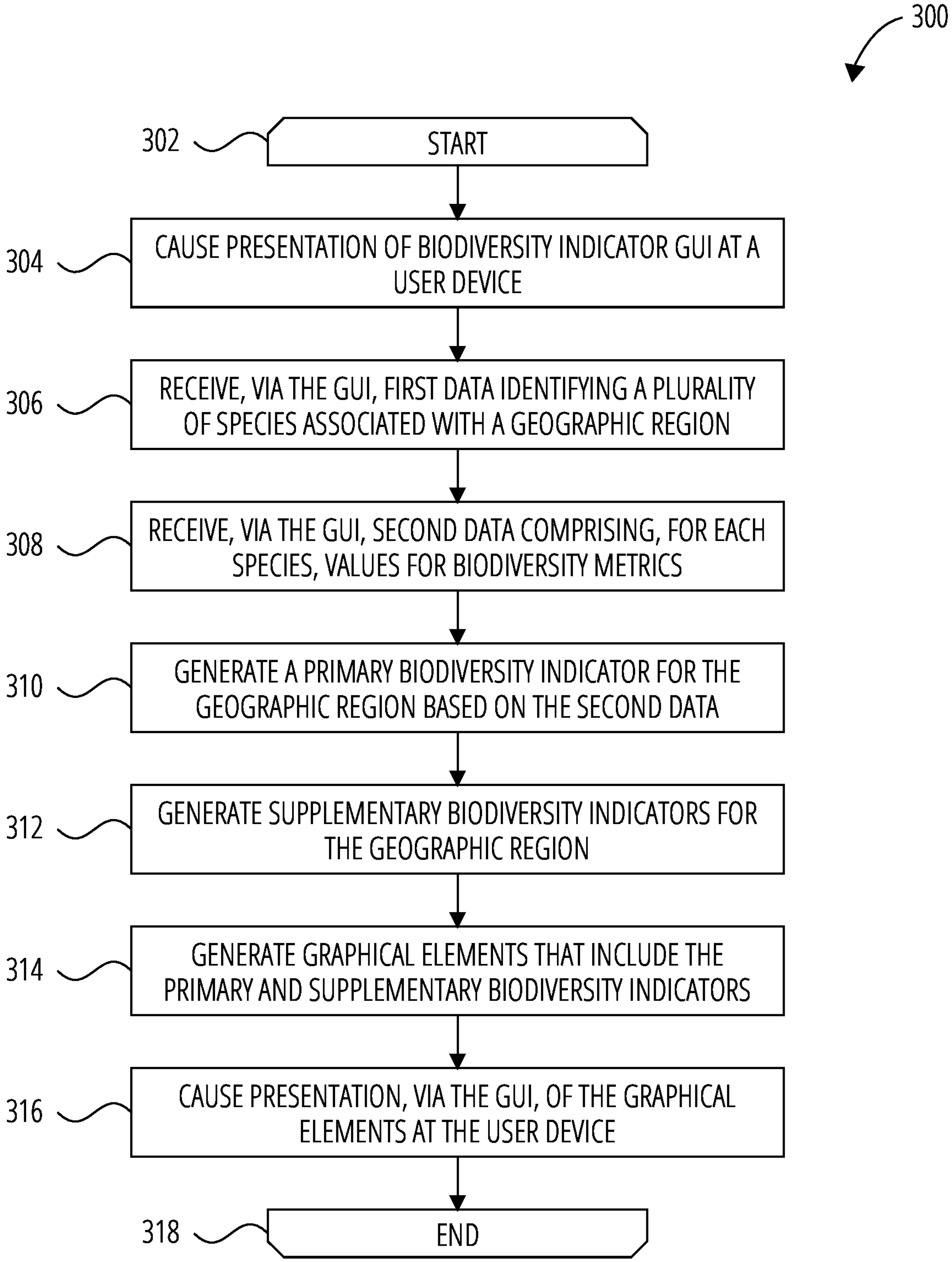
FIG. 3 is a flowchart illustrating a method suitable for generating a primary biodiversity indicator and supplementary biodiversity indicators, according to some examples.

FIG. 3 is a flowchart illustrating operations of a method 300 suitable for generating a primary biodiversity indicator and supplementary biodiversity indicators, according to some examples. By way of example and not limitation, aspects of the method 300 may be performed by the modules, components or databases shown in FIGS. 1 and 2.

The method 300 commences at opening loop element 302, and proceeds to operation 304, where the presentation module 210 causes presentation of a biodiversity indicator GUI at the user device 106. The GUI may be provided by the biodiversity indicator application, or any other software loaded or executable on a user device. The GUI enables the user 128 to make various selections, such as selecting details of the geographic region (e.g., name, size, type of environment, or the like), to provide or select a listing of species to associate with the geographic region, and to provide or select a category of each species. For example, each species may be categorized into one, or a combination of, categories, such as fauna, flora, land, air, water, ocean, migratory, or invasive species. The user 128 may also input or select a historic date as a "baseline," e.g., to allow the biodiversity indicator system 122 to automatically compare historic biodiversity in the geographic region with current biodiversity.

The input data module 204 receives first data that includes at least a listing of species to associate with the geographic region (operation 306) and, in response thereto, the presentation module 210 enables the user 128 to input second data via the GUI (operation 308). The second data includes one or more values of biodiversity metrics. Specifically, in some examples, the values include, for at least one of the biodiversity metrics, a reference value, and a current value. The reference value represents a historic value of the particular biodiversity metric, e.g., at a determinable date such as the historic date referred to above.

In some examples, at least some of the second data is input by the user 128. At least some of the second data may be accessed by the biodiversity indicator system 122 from another source or component.

The biodiversity metrics considered or processed within the biodiversity indicator system 122 may include at least one of: an abundance metric, a bio-dominance metric, a scarcity metric, a migration metric, a permanence metric, an overpopulation metric, a species richness metric, or an evenness metric. Non-limiting, illustrative examples of these metrics are provided below:

Abundance: the population of a particular species (e.g., elephants) in a specified geographic region.

Bio-dominance: the biomass of a particular species (e.g., elephants) in a specified geographic region, obtained by multiplying the population of the species by average mass.

Scarcity: a relative value (e.g., on a scale of 1 to 10) indicating how scarce a particular species is.

Migration: whether a particular species is migratory with respect to a specified geographic region and, if so, data relating to migration patterns.

Permanence: data indicating the presence or absence of a particular species within a specified geographic region over a period of time (e.g., percentage of years present, out of a set number of years).

Overpopulation: a percentage by which a species population in a specified geographic region exceeds carrying capacity.

Species richness: the number of unique species in a specified geographic region.

Evenness: data indicating how evenly individuals are distributed among different species (e.g., distribution of different tree species).

Other biodiversity metrics in the context of this disclosure may include indices, such as Simpson's Diversity Index. For example, for each species provided or selected by the user 128, the user may input or select a value of three biodiversity metrics: abundance, bio-dominance, and scarcity. These metrics are described further below. It should be appreciated that these metrics are merely examples, and that other metrics, or combinations of metrics, may be employed in other examples.

The method 300 proceeds to operation 310, where the biodiversity indicator system 122 generates a primary biodiversity indicator for the geographic region. This primary biodiversity indicator provides a numerical representation of overall biodiversity in the geographic region, and is based on the second data received at operation 308, e.g., the values of the included biodiversity metrics, as processed by the biodiversity indicator system 122. In some examples, the primary biodiversity indicator is a numerical index value expressed as a percentage of a reference indicator, e.g., the reference indicator may have a fixed value of "100," representing the biodiversity at the historic date, while the primary biodiversity indicator is expressed as a percentage thereof. For example, a primary biodiversity indicator of 65%, or "65 out of 100," may be interpreted to indicate that 35% of biodiversity within the specified geographic region has been lost since the historic date. A more detailed, non-limiting example of the generation of a primary biodiversity indicator is described below, with reference to FIGS. 4-8.

In some examples, and as shown at operation 312 in FIG. 3, the method 300 may also include generating one or more supplementary biodiversity indicators. For example, in addition to the primary biodiversity indicator that is calculated based on all the biodiversity metrics considered by the biodiversity indicator system 122, a supplementary biodiversity indicator may focus on one or more specific elements, or aspects, of biodiversity within the geographic region. For example, based on the user input provided by the user 128 via the GUI, the biodiversity indicator system 122 may generate supplementary indicators in the example forms of a species richness value and a concentration indicator (e.g., an indicator of biomass per unit area). The non-limiting example described below, with reference to FIGS. 4-8, provides more detail with respect to the generation of example supplementary biodiversity indicators.

Still referring to FIG. 3, once the primary and supplementary biodiversity indicators have been generated (e.g., by the processing module 208), the presentation module 210 may automatically generate, within the GUI, a set of graphical elements that include the primary and supplementary biodiversity indicators (operation 314). At operation 316, these graphical elements are caused to be presented at the user device 106, e.g., within the GUI. The presentation module 210 may cause the graphical elements to be visually distinguished from each other (e.g., through the use of different colors, sizes, or other interface elements) to provide meaningful and understanding output. The method 300 concludes at closing loop element 318.

Turning now to FIGS. 4-8, a GUI 402 of a biodiversity indicator application is shown in these figures, according to some examples. In FIGS. 4-8, the GUI 402 is presented on the app interface 132 of the programmatic client 108 of the user device 106, e.g., a laptop or desktop computer. It will be appreciated that some functions of the biodiversity indicator system 122 may be performed client-side, while others may be performed server-side. It will also be appreciated that the presentation of the GUI on the app interface 132 is a non-limiting example, and GUIs according to examples of the present disclosure may be presented on any suitable device or in any suitable format.

Figure 4:
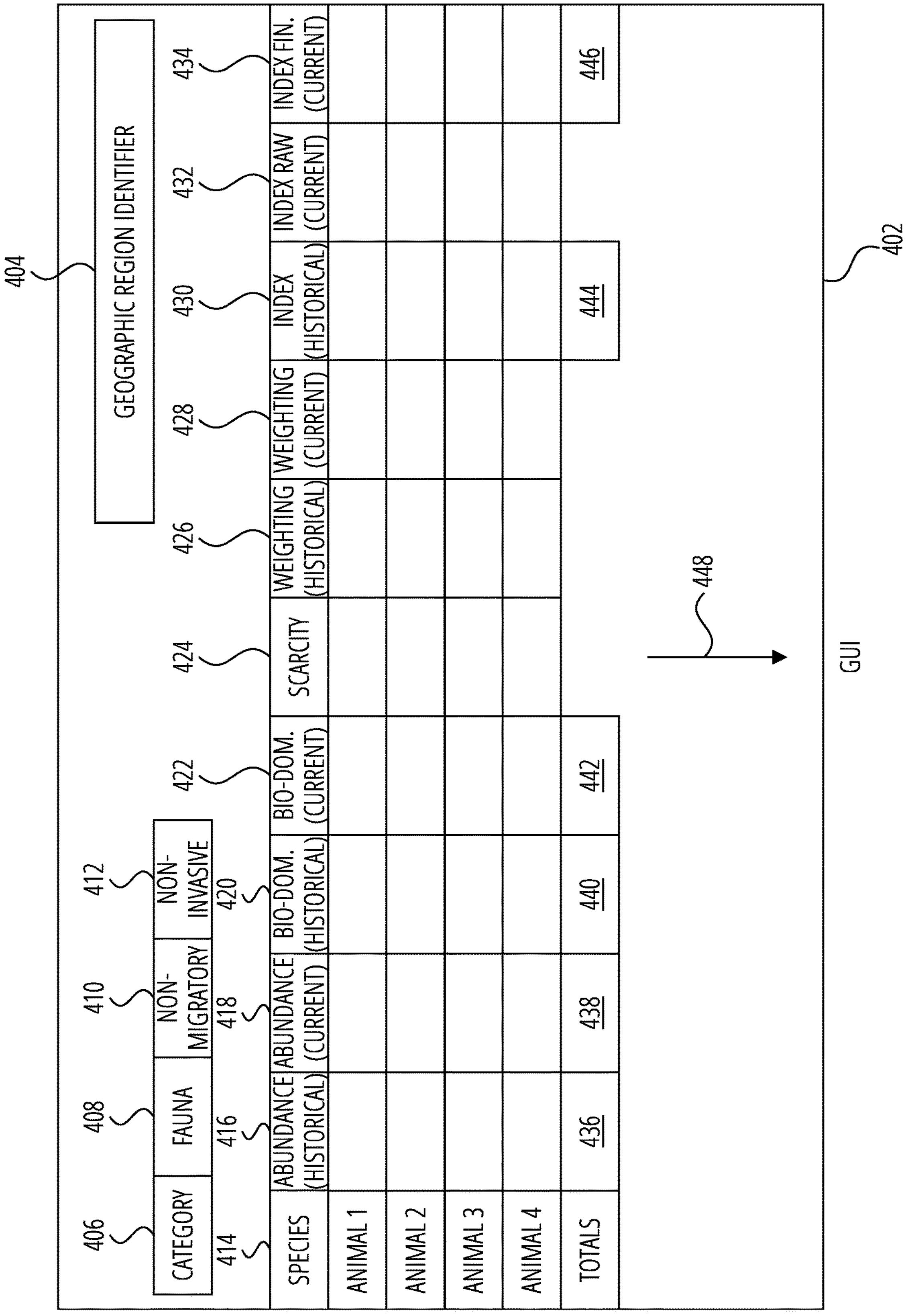
FIG. 4 is a user interface diagram illustrating a graphical user interface (GUI) used to facilitate generation of biodiversity indicators, wherein a first category of species is shown, according to some examples.

Referring, firstly, to FIG. 4, the GUI 402 includes several graphical interface elements. Some of the interface elements enable the user 128 to provide user input, e.g., through inputting of data or making selections, while other interface elements are not user-selectable or user-adjustable, and are automatically updated by the biodiversity indicator system 122, as described below.

The GUI 402 includes a geographic region identifier 404 that identifies the current geographic region which the user 128 is viewing or editing. For example, the geographic region identifier 404 may include a name of a property or region, and a location of the property or region. The GUI 402 further includes a category section 406 that enables the user 128 to select a category of species to add to the geographic region, or to categorize an already added list of species. In the GUI 402, a primary category indicator 408, a migration indicator 410, and an invasiveness indicator 412 can all be adjusted or selected in order to define the category of species. In FIG. 4, a first category is shown. The first category includes only non-migratory, non-invasive animals. The user 128 thus adjusts the primary category indicator 408 to indicate "fauna," the migration indicator 410 to indicate "non-migratory," and the invasiveness indicator 412 to indicate "non-invasive." In some examples, the category section 406 may enable the user 128 to specify the type of animal in more detail, e.g., "land" or "air," and different types of non-migratory, non-invasive animals may thus be grouped into different categories.

Returning to FIG. 4, the user 128 then proceeds to add a listing of species ("Animal 1" to "Animal 4") to the first category, in a species section 414. It will be appreciated that the number of species added will depend on the environment and region, and four animals is merely shown as an example.

It may be desirable to identify all, or as many as possible, species falling within a particular category, and upload the relevant data to the biodiversity indicator system 122 in order to cause generation of an accurate final representation.

For each species, the user 128 inputs a value for historical abundance 416, current abundance 418, historical bio-dominance 420, current bio-dominance 422, and scarcity 424. Accordingly, in this example, the biodiversity indicator system 122 utilizes three biodiversity metrics: abundance, bio-dominance, and scarcity. The historic values are reference values, e.g., baseline values as at a historic date, while the current values are values used to define the geographic region at a different date (e.g., a current point in time).

The historical abundance 416 and current abundance 418 may be represented as the number (physical quantity, e.g., population) of each species in the geographic region, at a defined historic date and a current date, respectively. The number may be a counted number or estimated (e.g., extrapolated) number. The historical bio-dominance 420 and the current bio-dominance 422 may be represented as the total biomass of each species at the historic date and the current date, respectively. For example, bio-dominance may be calculated in a similar manner to biomass, such as by multiplying the abundance value by an average mass of a particular species. In other words, the historical bio-dominance 420 for "Animal 1" may automatically be calculated by the biodiversity indicator system 122 by multiplying the historical abundance 416 by a mass value, or it may be provided by the user 128. Similarly, the current bio-dominance 422 for "Animal 1" may be automatically calculated by the biodiversity indicator system 122 by multiplying the current abundance 418 by the same mass value, or it may be provided by the user 128.

Once the historical abundance 416, current abundance 418, historical bio-dominance 420, and current bio-dominance 422 values have been populated or selected, the biodiversity indicator system 122 automatically generates and presents a total historical abundance 436, a total current abundance 438, a total historical bio-dominance 440, and a total current bio-dominance 442, for the first category, in the blocks shown in FIG. 4. In this example, each "total" is the sum of the individual values of each biodiversity metric within the category, as depicted below for total historical abundance 436, as an example:

$$\text{Total Historical Abundance for Category} = \sum_{i=1}^{n} \text{Historical Abundance of Species } n$$

It is noted that only a "current" scarcity value is employed in the GUI 402 of FIG. 4. Thus, the user 128 may input the latest value or score for scarcity 424 of each species in the relevant block in the GUI 402. Alternatively, the biodiversity indicator system 122 may auto-populate the scarcity 424 with the latest data from the database 126 or a third-party server 112 once the user 128 has selected the species in the species section 414. Scarcity may mirror, or be based on, official values, e.g., those provided or approved from time to time in terms of international agreements, such as CITES (Convention on International Trade in Endangered Species of Wild Fauna and Flora), or maintained by an international body, such as the International Union for Conservation of Nature (IUCN). In this example the value for scarcity 424 of "Animal 1" to "Animal 4" may each be represented as a score of between 1 and 50, with 50 being the scarcest. In this way, a species that is scarcer than another species may have a greater relative downstream impact on the value of the final biodiversity indicator for the geographic region.

The biodiversity indicator system 122 then automatically generates a reference weighting coefficient 426 (e.g., a baseline weighting) and a current weighting coefficient 428 for each species the first category and presents the values in the blocks shown in FIG. 4. These coefficients are calculated as follows, for each individual species, where "BD" is bio-dominance, "RWC" is Reference Weighting Coefficient and "CWC" is Current Weighting Coefficient.

$$RWC = \frac{\text{Species Historical Abundance} + \text{Species Historical } BD}{\text{Total Historical Abundance of Category} + \text{Total Historical } BD \text{ of Category}}$$

$$CWC = \frac{\text{Species Current Abundance} + \text{Species Current } BD}{\text{Total Current Abundance of Category} + \text{Total Current } BD \text{ of Category}}$$

The weighting coefficient is generated so as to assign a weighting factor to each species in the geographic region, both at the historic date and the current date. The biodiversity indicator system 122 then generates a reference index value 430 and a raw current index value 432 for each species. In this example, the reference index value 430 and the raw current index value 432 are calculated as follows, for each species, where "RIV" is Reference Index Value and "CIV" is Current Index Value:

$$RIV \text{ for Species} = \text{Species Reference Weighting Coefficient} \times \text{Species Scarcity}$$

$$CIV \text{ for Species (Raw)} = \text{Species Current Weighting Coefficient} \times \text{Species Scarcity}$$

The raw current index value 432 is referred to as a "raw" value, because, in some examples, one or more penalties or other adjustments may be applied to change the raw current index value 432 before reaching a final current index value 434 for a particular species. For example, during generation of the current index value for each respective species, the biodiversity indicator system 122 may determine whether to apply a penalty to the (raw) current index value based on whether a penalty criterion is met for the respective species. In some examples, the penalty criterion is met if the current value of the abundance metric for the respective species exceeds the reference value (e.g., historic value) of the abundance metric for the same species (e.g., by a threshold value). In the case of over-abundance, the penalty condition may cause invocation of an overweighting limiting formula. Pseudocode for implementing the penalty is provided below, as a non-limiting example:

```
start
  if Species_Current_Abundance > Species_Historical_Abundance
     Final_Current_Index_Value = Raw_Current_Index_Value −
((int(Species_Current_Abundance / 5) * 1.3) +
((Species_Current_BioDominance −
Species_Historical_BioDominance) * 0.01))
  else
       Final_Current_Index_Value = Raw_Current_Index_Value
end
```

Therefore, if a penalty condition exists, the raw current index value 432 may be more than the final current index value 434. If no penalty condition exists, the final current index value 434 may be set as equal to the raw current index value 432. Then, the biodiversity indicator system 122 aggregates the reference index values 430 for all the species in the first category by calculating the sum of all these values, thus arriving at a total reference index value 444. Similarly, the biodiversity indicator system 122 aggregates the final current index values 434 for all the species in the first category by calculating the sum of all these values, thus arriving at a total current index value 446. The data relating to the first category, as shown in FIG. 4, is stored by the storage module 212, e.g., in the database 126 or in a local storage component of the user device 106.

In some examples, only a single category of species may be defined. In such cases, a primary biodiversity indicator for the geographic region may be determined by expressing the total current index value 446 as a percentage or fraction of the total reference index value 444 (e.g., the total "baseline" value at the historic date) for the category. However, in other examples, and as is the case in FIGS. 4-8, multiple categories are defined and are all taken into account to generate the primary biodiversity indicator. As indicated by the arrow 448, the user 128 may navigate within the GUI 402, e.g., by scrolling down to define or adjust values of a second category.

Figure 5:
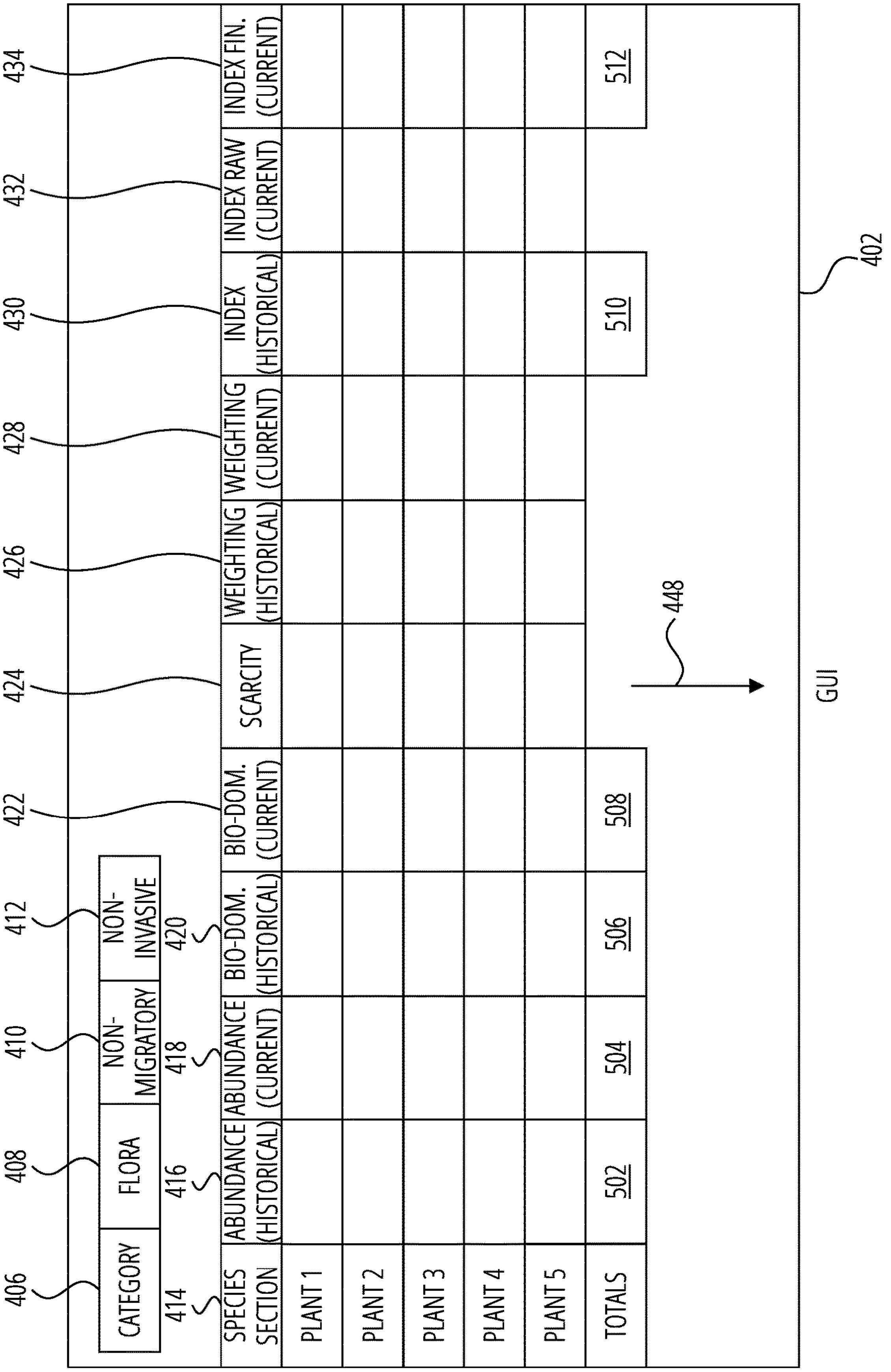
FIG. 5 is a user interface diagram illustrating a GUI used to facilitate generation of biodiversity indicators, wherein a second category of species is shown, according to some examples.

In FIG. 5, the GUI 402 illustrates the second category of species selected by the user 128: non-migratory, non-invasive plants. The user 128 selects or adjusts the primary category indicator 408 to indicate "flora," the migration indicator 410 to indicate "non-migratory," and the invasiveness indicator 412 to indicate "non-invasive."

The user 128 then proceeds to add a listing of species ("Plant 1" to "Plant 5") to the second category, in the species section 414. For each species, the user 128 inputs or selects a value for historical abundance 416, current abundance 418, historical bio-dominance 420, current bio-dominance 422, and scarcity 424, as described with reference to FIG. 4. As explained, certain values (such as bio-dominance or scarcity) may be automatically populated by the biodiversity indicator system 122.

The biodiversity indicator system 122 automatically generates and presents a total historical abundance 502, a total current abundance 504, a total historical bio-dominance 506, and a total current bio-dominance 508, for the second category of species shown in FIG. 5. These totals are calculated in the same manner as in FIG. 4.

Then, the biodiversity indicator system 122 generates the reference index value 430 and the final current index value 434 for each species in the second category, in the same manner as in FIG. 4, and aggregates the respective values (by summing them) to obtain a total reference index value 510, and a total current index value 512 for the second category. The data relating to the second category, as shown in FIG. 5, is stored by the storage module 212, e.g., in the database 126 or in a local storage component of the user device 106.

Figure 6:
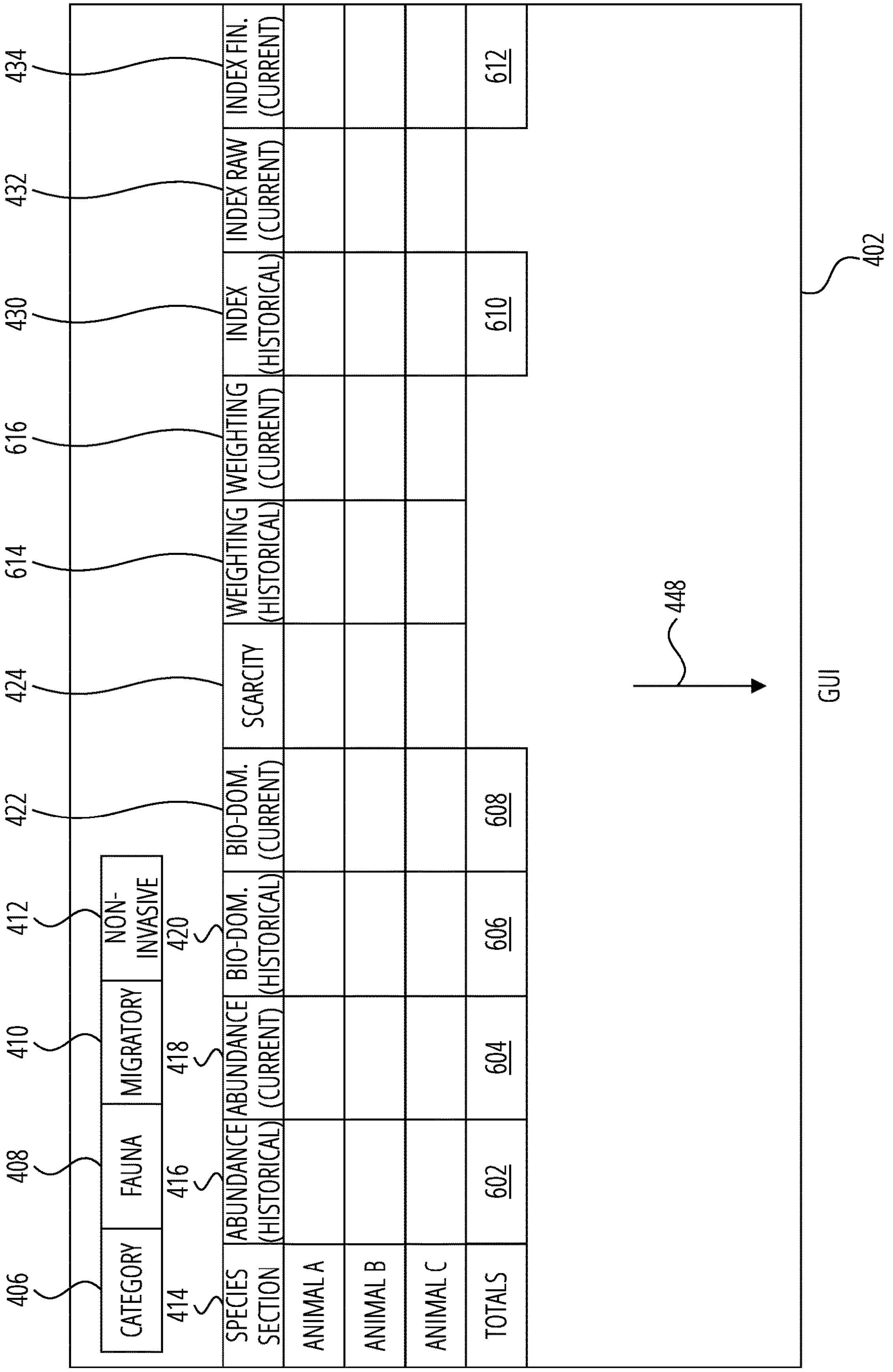
FIG. 6 is a user interface diagram illustrating a GUI used to facilitate generation of biodiversity indicators, wherein a third category of species is shown, according to some examples.

The user 128 then navigates to a third category. In FIG. 6, the GUI 402 illustrates the third category of species selected by the user 128: migratory, non-invasive animals. The user 128 selects or adjusts the primary category indicator 408 within the GUI to indicate "fauna," the migration indicator 410 to indicate "migratory," and the invasiveness indicator 412 to indicate "non-invasive." In some examples, the category section 406 may enable the user 128 to specify the type of migratory animal in more detail, e.g., "water" or "land," and different types of migratory, non-invasive animals may thus be grouped into different categories.

Returning to FIG. 6, the reference index value 430 and the final current index value 434 are determined by the biodiversity indicator system 122 in a different manner for migratory species compared to non-migratory species, as will become apparent from the description that follows. The user 128 proceeds to add a listing of migratory species ("Animal A" to "Animal C") to the third category, in the species section 414. For each species, the user 128 inputs or selects a value for historical abundance 416, current abundance 418, historical bio-dominance 420, current bio-dominance 422, and scarcity 424. It is noted that the animals in FIG. 4 and the animals in FIG. 6 are not necessarily mutually exclusive from a species perspective, e.g., the geographic region may have first group of elephants that reside within the geographic region permanently (thus included in the first category), while a second group of elephants migrate out of the geographic region for half of the year (this included in the third category).

The biodiversity indicator system 122 automatically generates and presents a total historical abundance 602, a total current abundance 604, a total historical bio-dominance 606, and a total current bio-dominance 608, for the third category of species shown in FIG. 6. These totals are calculated in the same manner as in FIG. 4.

Then, the biodiversity indicator system 122 generates the reference index value 430 and the final current index value 434 for each species in the third category, in the same manner as in FIG. 4, but for one difference: in response to detecting that the animals are categorized as migratory, the biodiversity indicator system 122 applies a reduced weighting coefficient (both historical and current) to the animals in the third category. In this example, the biodiversity indicator system 122 assumes that "Animal A" to "Animal C" are present in the geographic region for only 50% of the time, and thus halves each weighting coefficient (the reference weighting coefficient 614 and the current weighting coefficient 616) compared to the coefficients used for non-migratory species, as indicated by the two equations below. However, other reductions may be applied in some examples, e.g., based on a specific user input indicating the percentage of time the respective species spends within the geographic region. Below, "BD" again refers to bio-dominance, "RWC" to Reference Weighting Coefficient, and "CWC" to Current Weighting Coefficient.

$$RWC = \frac{\left(\frac{\text{Species Historical Abundance} + \text{Species Historical } BD}{\text{Total Historical Abundance of Category} + \text{Total Historical } BD \text{ of Category}}\right)}{2}$$

$$CWC = \frac{\left(\frac{\text{Species Current Abundance} + \text{Species Current } BD}{\text{Total Current Abundance of Category} + \text{Total Current } BD \text{ of Category}}\right)}{2}$$

The respective index values are aggregated (by summing them) to obtain a total reference index value 610 and a total current index value 612 for the third category. The data relating to the third category, as shown in FIG. 6, is stored by the storage module 212, e.g., in the database 126 or in a local storage component of the user device 106.

Figure 7:
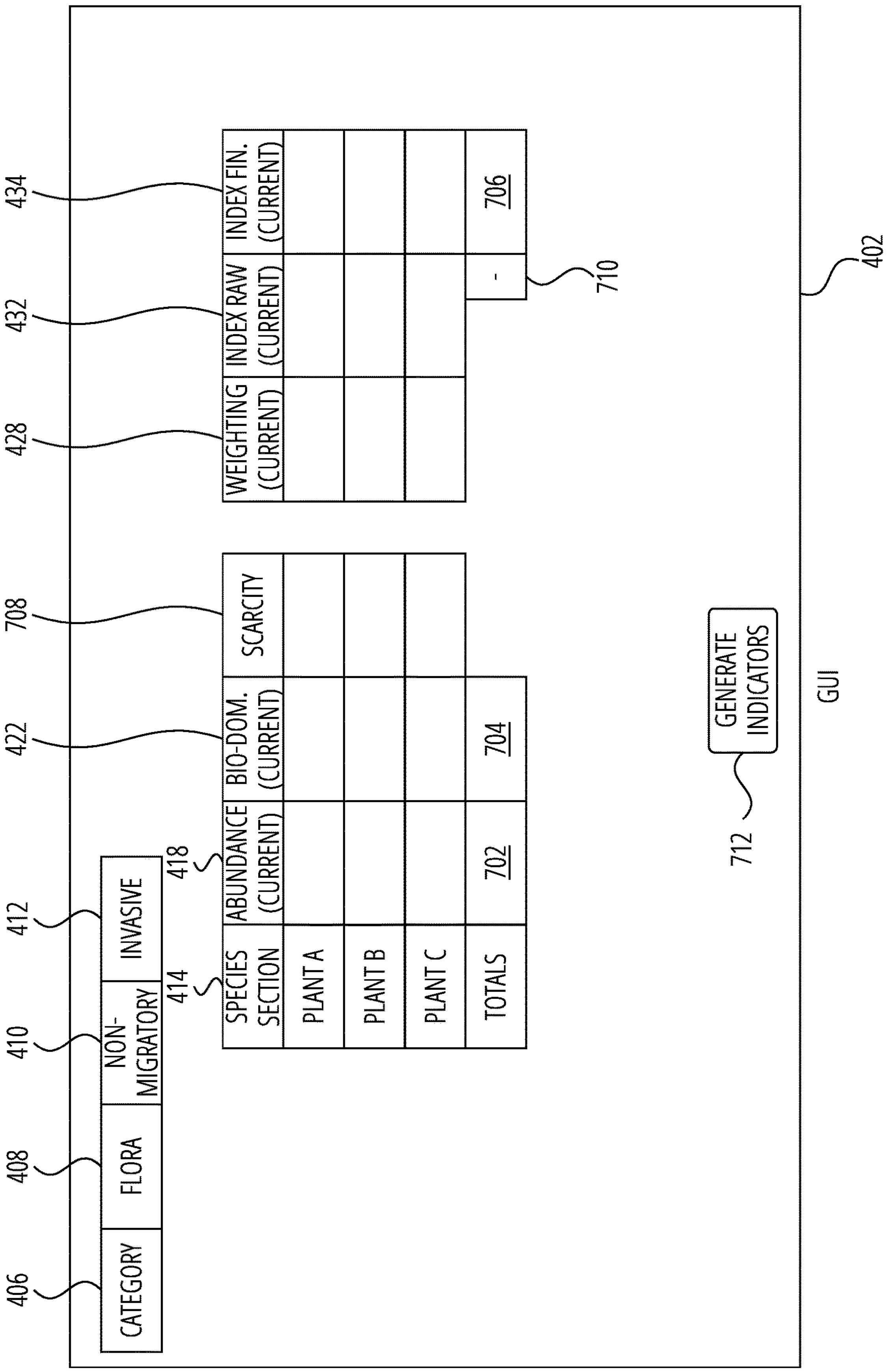
FIG. 7 is a user interface diagram illustrating a GUI used to facilitate generation of biodiversity indicators, wherein a fourth category of species is shown, according to some examples.

The user 128 then navigates to a fourth category. In FIG. 7, the GUI 402 illustrates the fourth category of species selected by the user 128: non-migratory, invasive plants. The user 128 selects or adjusts the primary category indicator 408 within the GUI to indicate "flora," the migration indicator 410 to indicate "non-migratory," and the invasiveness indicator 412 to indicate "invasive." The raw current index value 432 and final current index value 434 are determined differently for invasive species than for non-invasive species. Specifically, in this example, the index values are deemed "penalty values" and expressed as negative values, while the index values for non-invasive species (as in FIG. 4, FIG. 5, and FIG. 6) are positive values. Further, when a user selects or inputs an invasive species, the GUI 402 does not present or generate reference values (e.g., "historical" or "baseline" values).

Referring specifically to FIG. 7, the user 128 proceeds to add a listing of invasive species ("Plant A" to "Plant C") to the fourth category, in the species section 414. For each species, the user 128 inputs or selects a value for current abundance 418, current bio-dominance 422, and scarcity, in the blocks provided. As mentioned, and given that the species in FIG. 7 (fourth category) are invasive, the biodiversity indicator system 122 does not require reference values (because the species may not have been "historically" occurring within the geographic region). As is the case in FIG. 4, FIG. 5, and FIG. 6, the scarcity value is a current value. However, in some examples, for invasive species, the scarcity value may be expressed as a scarcity penalty 708 to indicate harm or potential harm caused by the species in the geographic region. A higher scarcity penalty 708 may indicate greater harm or potential harm.

The biodiversity indicator system 122 automatically generates and presents a total current abundance 702 and a total current bio-dominance 704, for the fourth category of species shown in FIG. 7. These totals are calculated in the same manner as in FIG. 4. Then, the biodiversity indicator system 122 generates the final current index value 434 for each species in the fourth category, in the same manner as in FIG. 4, but for one difference: in response to detecting that the plants are categorized as invasive, the biodiversity indicator system 122 adjusts the raw current index value 432 to transform it to a penalty, e.g., by multiplying it by −1 (negative one).

Thus, the final current index value 434 is a negative value that is intended to cause an automatic reduction in the primary biodiversity indicator for the geographic region, as further described below. The final current index value 434 for all the invasive species in the category are aggregated (by summing them) to obtain a total current index value 706 for the third category. The penalty indicator 710 in FIG. 7 indicates that this is expressed as a negative value. The data relating to the fourth category, as shown in FIG. 7, is stored by the storage module 212, e.g., in the database 126 or in a local storage component of the user device 106.

As mentioned above, a primary biodiversity indicator may be automatically generated for the geographic region. In some examples, the primary biodiversity indicator is calculated by the biodiversity indicator system 122 by aggregating all the current index values, e.g., in the example of the GUI 402, adding the total current index value 446, the total current index value 512, the total current index value 612, and the total current index value 706, to each other, to obtain a "current biodiversity index score" for the geographic region. It is noted that, for invasive species, the current index values will reduce the current biodiversity index score, e.g., the total current index value 706 will cause a reduction in the total, as it is a negative value.

In order to express the current biodiversity index score in a meaningful manner, it can be represented as a percentage of a reference biodiversity index score. The biodiversity indicator system 122 may convert the biodiversity indicator from a non-standardized format to a standardized format for presentation within the GUI. This action may automatically be performed by the biodiversity indicator system 122 by aggregating all the reference index values, e.g., in the example of the GUI 402, adding the total reference index value 444, the total reference index value 510 and the total reference index value 610, to each other (with the invasive species category of FIG. 7 having no reference values). For example, if the total of the current index values for all categories is 50,000, and the total of the reference index values for all categories is 70,000, the final primary biodiversity indicator (BI) may be determined as shown in the example below.

$$BI = \frac{\sum \text{Current index values}}{\sum \text{Reference index values}} \times 100$$

$$BI = \frac{50{,}000}{70{,}000} \times 100 = 71.43\%$$

Figure 8:
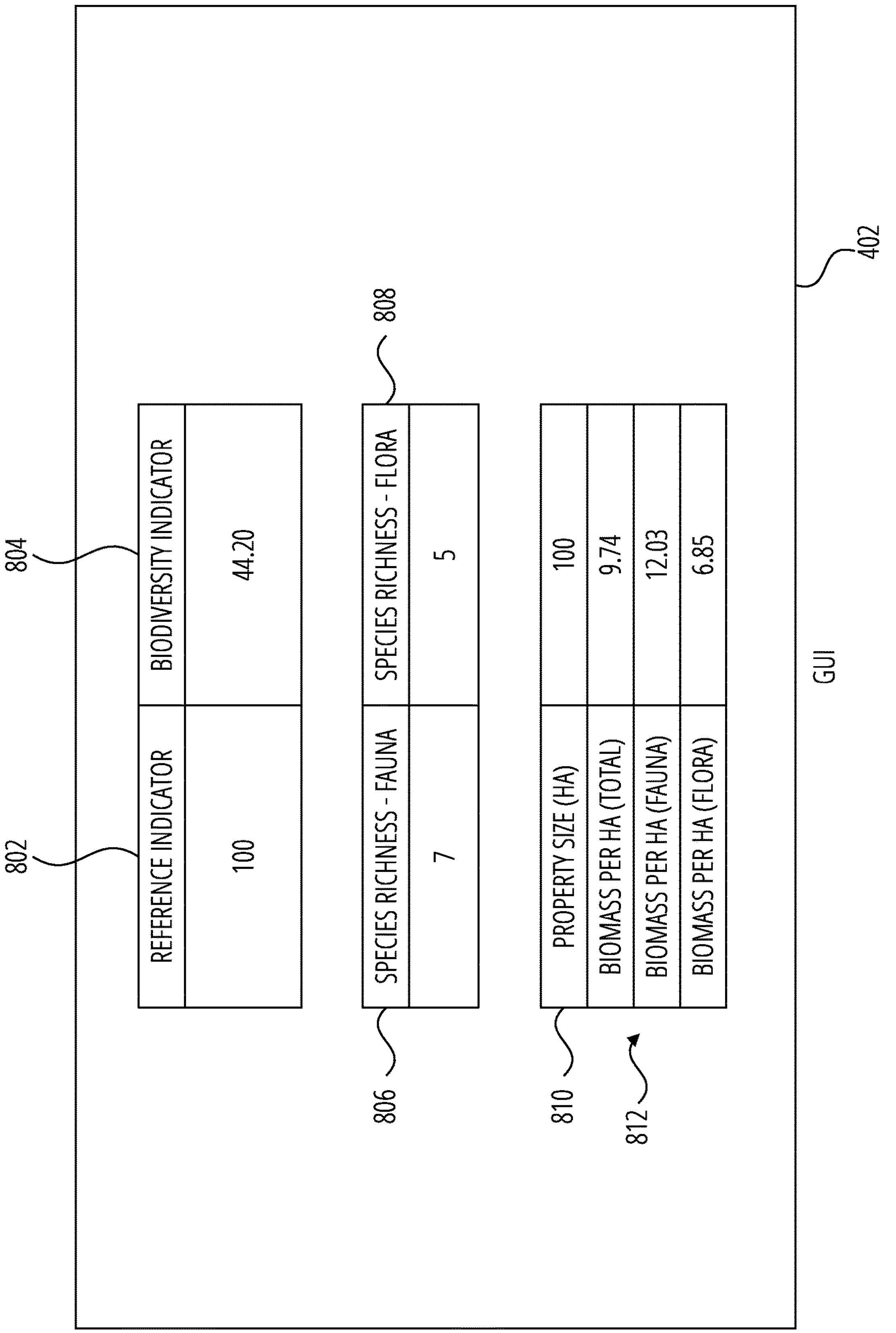
FIG. 8 is a user interface diagram illustrating a GUI used to facilitate generation of biodiversity indicators, wherein a set of biodiversity indicators is presented, according to some examples.

Thus, instead of presenting the BI as an "arbitrary" value of 50,000 that may be difficult to interpret, it is converted to a standardized format by automatically comparing the current biodiversity index score with the reference biodiversity index score to obtain a standardized biodiversity indicator. FIG. 8 further illustrates the GUI 402 when presenting a set of biodiversity indicators, according to some examples. In FIG. 8, the GUI 402 presents a first graphical element in the form of a primary biodiversity indicator 804, adjacent to a second graphical element in the form of a reference indicator 802 which is fixed at "100." This is intended to reflect the change in biodiversity as compared to the historic date associated with the reference indicator 802.

In some examples, the GUI 402 may also present the historic date in association with the reference indicator 802 and a current date in association with the primary biodiversity indicator 804. In the example of FIG. 8, the value of 44.20 (44.20%) may be interpreted by the user 128 to indicate, or imply, that the geographic region in question has been degraded by 55.80% from a biodiversity perspective, in the context of the biodiversity metrics included in the analysis, as well as the weights and penalties (if any) applied.

The biodiversity indicator system 122 may visually distinguish presentation of the reference indicator 802 and the primary biodiversity indicator 804, e.g., by displaying them in different colors. In some examples, the color of the graphical element presenting the primary biodiversity indicator 804 may be based on the severity of degradation, e.g., the primary biodiversity indicator 804 may be shown in red if the percentage is below 50%, in orange if it is from 50% to 75%, and in green if it is greater than 75%.

As mentioned above, the biodiversity indicator system 122 may also generate one or more supplementary biodiversity indicators. In FIG. 8, the GUI 402 includes a third graphical element that presents a value for species richness 806 of fauna within the geographic region and a value for species richness 808 of flora within the geographic region. These values may, for example, be the total number of animals and plants, respectively, input by the user 128 (disregarding any invasive species).

Further, the GUI 402 includes a fourth graphical element presenting a set of concentration indicators 812 in the example form of "biomass per hectare" values for the geographic region (expressed in kilogram per hectare). The user 128 may input or select the size of the geographic region, e.g., add the property size 810 in the block provided, and the biodiversity indicator system 122 may automatically calculate and present the concentration indicators 812. For example, the "biomass per hectare" may be calculated as the total of all current bio-dominance values (where bio-dominance values are expressed in kilograms) divided by the property size 810. As shown in FIG. 8, this may be broken down by species type, e.g., fauna and flora.

As alluded to above, a biodiversity indicator may be associated with, or expressed as, a monetary value. For example, the GUI 402 may include a further graphical element presenting a single or a set of monetary value indicators, e.g., enabling the user to compare or assess a reference monetary value against a current monetary value. A monetary value biodiversity indicator may be generated in a variety of ways. For example, the biodiversity indicator system 122 may receive user input (or obtain from another source) monetary values associated with each respective species, both historic and current. For each species, the biodiversity indicator system 122 may then generate a historic species monetary value by multiplying the historic abundance of the species by the historic monetary value, and a current species monetary value by multiplying the current abundance of the species by the current monetary value. The biodiversity indicator system 122 may then obtain a reference index score or value which is the total historic monetary value of the listed species (or a defined subset of the species for which monetary values are available), and a current index score or value which is the total current monetary value of the listed species (or the defined subset). The GUI 402 may thus present a monetary value associated with species in the geographic region as a biodiversity indicator. In some examples, the GUI 402 automatically expresses the current monetary value as a percentage or factor of the reference monetary value to provide a useful visual comparison.

In some examples, irrespective of whether monetary values are used in the generation of the biodiversity indicators, monetary values may be used as a downstream tool. For example, if the final primary biodiversity indicator shows a value of 52%, this could equal a monetary amount such as $52,000.00, assisting, for example, in issuing of credits or options. In the "52%" and "$52,000.00" example, "biodiversity credits" could be issued in association with a specific region at, for instance, $1.00 each and sold at $0.52, based on a current biodiversity value.

The GUI 402 may include a user-selectable element, such as a generate indicators button 712 which is shown in FIG. 7, that is selectable by the user 128 to cause, or finalize, generation of the biodiversity indicators by the biodiversity indicator system 122 and presentation thereof within the GUI 402. In other examples, the biodiversity indicators may simply be automatically generated and adjusted as the user 128 adds or adjusts information in the GUI, and the user may navigate the biodiversity indicator application to view the biodiversity indicators.

In some examples, the biodiversity indicator application may provide additional output data. For example, the user 128 may specify multiple "reference points," each relating to a different date, thus allowing the biodiversity indicator application to generate multiple reference indicators based on different sets of reference values, e.g., in order to output a graph that displays changes in biodiversity over time within a geographic region.

The user 128 may, in some examples, access the biodiversity indicator application remotely via the network 102 to update values within the GUI 402, or add further values (e.g., add species found within the geographic region), thus causing automated updating of the biodiversity indicators.

Figure 9:
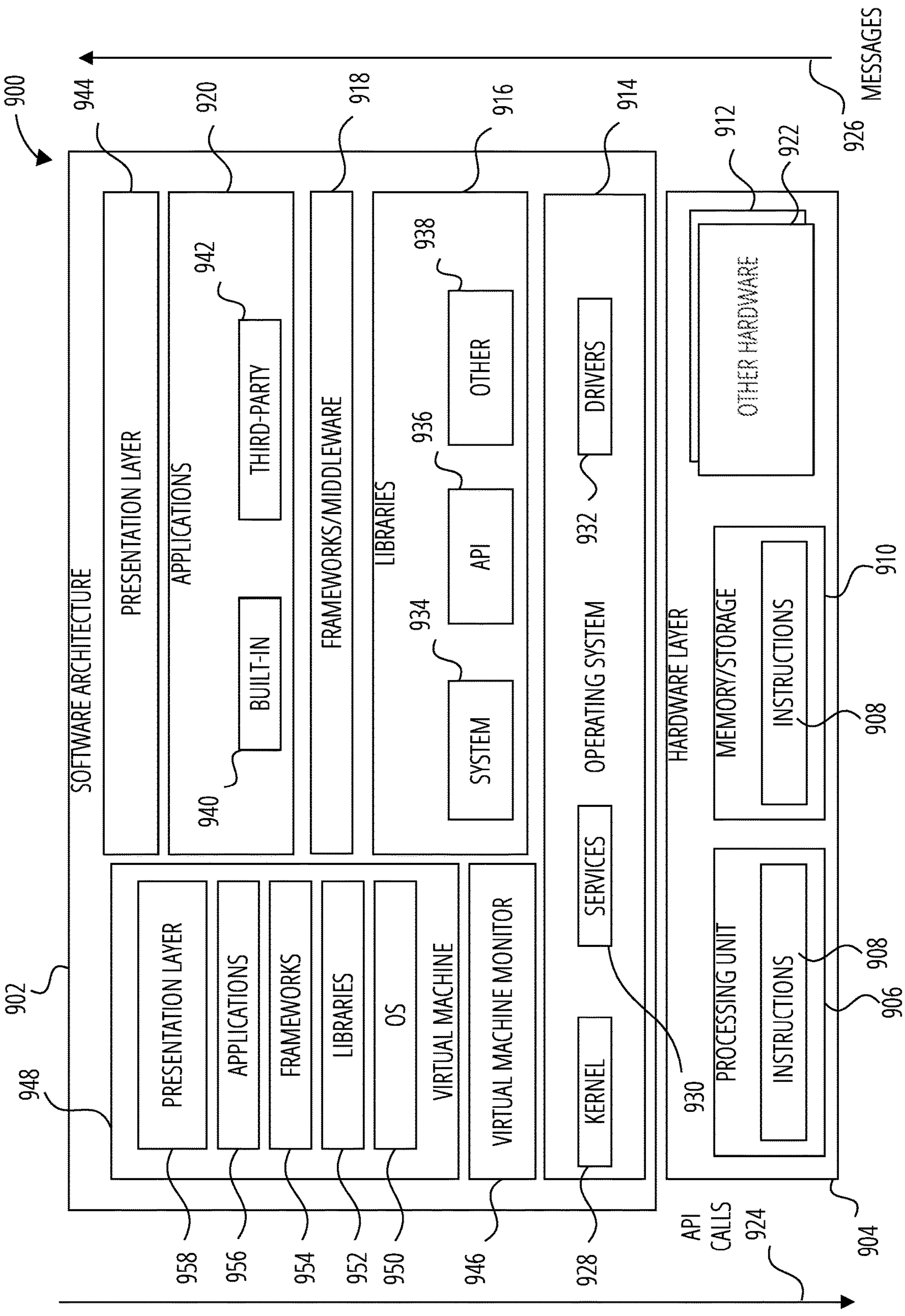
FIG. 9 is a block diagram showing a software architecture for a computing device, according to some examples.

FIG. 9 is a block diagram 900 showing a software architecture 902 for a computing device, according to some examples. The software architecture 902 may be used in conjunction with various hardware architectures, for example, as described herein. FIG. 9 is merely a non-limiting illustration of a software architecture, and many other architectures may be implemented to facilitate the functionality described herein. A representative hardware layer 904 is illustrated and can represent, for example, any of the above referenced computing devices. In some examples, the hardware layer 904 may be implemented according to the architecture of the computer system of FIG. 10.

The representative hardware layer 904 comprises one or more processing units 906 having associated executable instructions 908. Executable instructions 908 represent the executable instructions of the software architecture 902, including implementation of the methods, modules, subsystems, and components, and so forth described herein and may also include memory and/or storage modules 910, which also have executable instructions 908. Hardware layer 904 may also comprise other hardware as indicated by other hardware 912 and other hardware 922 which represent any other hardware of the hardware layer 904, such as the other hardware illustrated as part of the software architecture 902.

In the architecture of FIG. 9, the software architecture 902 may be conceptualized as a stack of layers where each layer provides particular functionality. For example, the software architecture 902 may include layers such as an operating system 914, libraries 916, frameworks/middleware layer 918, applications 920, and presentation layer 944.

Operationally, the applications 920 or other components within the layers may invoke API calls 924 through the software stack and access a response, returned values, and so forth illustrated as messages 926 in response to the API calls 924. The layers illustrated are representative in nature and not all software architectures have all layers. For example, some mobile or special purpose operating systems may not provide a frameworks/middleware layer 918, while others may provide such a layer. Other software architectures may include additional or different layers.

The operating system 914 may manage hardware resources and provide common services. The operating system 914 may include, for example, a kernel 928, services 930, and drivers 932. The kernel 928 may act as an abstraction layer between the hardware and the other software layers. For example, the kernel 928 may be responsible for memory management, processor management (e.g., scheduling), component management, networking, security settings, and so on. The services 930 may provide other common services for the other software layers. In some examples, the services 930 include an interrupt service. The interrupt service may detect the receipt of an interrupt and, in response, cause the software architecture 902 to pause its current processing and execute an interrupt service routine (ISR) when an interrupt is accessed.

The drivers 932 may be responsible for controlling or interfacing with the underlying hardware. For instance, the drivers 932 may include display drivers, camera drivers, Bluetooth® drivers, flash memory drivers, serial communication drivers (e.g., Universal Serial Bus (USB) drivers), Wi-Fi® drivers, near-field communication (NFC) drivers, audio drivers, power management drivers, and so forth depending on the hardware configuration.

The libraries 916 may provide a common infrastructure that may be utilized by the applications 920 or other components or layers. The libraries 916 typically provide functionality that allows other software modules to perform tasks in an easier fashion than to interface directly with the underlying operating system 914 functionality (e.g., kernel 928, services 930 or drivers 932). The libraries 916 may include system libraries 934 (e.g., C standard library) that may provide functions such as memory allocation functions, string manipulation functions, mathematic functions, and the like. In addition, the libraries 916 may include API libraries 936 such as media libraries (e.g., libraries to support presentation and manipulation of various media format such as MPEG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 916 may also include a wide variety of other libraries 938 to provide many other APIs to the applications 920 and other software components/modules.

The frameworks/middleware layer 918 may provide a higher-level common infrastructure that may be utilized by the applications 920 or other software components/modules. For example, the frameworks/middleware layer 918 may provide various graphic user interface (GUI) functions, high-level resource management, high-level location services, and so forth. The frameworks/middleware layer 918 may provide a broad spectrum of other APIs that may be utilized by the applications 920 or other software components/modules, some of which may be specific to a particular operating system or platform.

The applications 920 include built-in applications 940 or third-party applications 942. Examples of representative built-in applications 940 may include, but are not limited to, a contacts application, a browser application, a book reader application, a location application, a media application, a messaging application, or a game application. Third-party applications 942 may include any of the built-in applications as well as a broad assortment of other applications. In a specific example, the third-party application 942 (e.g., an application developed using the Android™ or iOS™ software development kit (SDK) by an entity other than the vendor of the particular platform) may be mobile software running on a mobile operating system such as iOS™, Android™, Windows® Phone, or other mobile computing device operating systems. In this example, the third-party application 942 may invoke the API calls 924 provided by the mobile operating system such as operating system 914 to facilitate functionality described herein.

The applications 920 may utilize built in operating system functions (e.g., kernel 928, services 930 or drivers 932), libraries (e.g., system libraries 934, API libraries 936, and other libraries 938), and frameworks/middleware layer 918 to create user interfaces to interact with users of the system. Alternatively, or additionally, in some systems, interactions with a user may occur through a presentation layer, such as presentation layer 944. In these systems, the application/module "logic" can be separated from the aspects of the application/module that interact with a user.

Some software architectures utilize virtual machines. In the example of FIG. 9, this is illustrated by virtual machine 948. A virtual machine creates a software environment where applications/modules can execute as if they were executing on a hardware computing device. A virtual machine is hosted by a host operating system (operating system 914) and typically, although not always, has a virtual machine monitor 946, which manages the operation of the virtual machine as well as the interface with the host operating system (e.g., operating system 914). A software architecture executes within the virtual machine 948 such as an operating system 950, libraries 952, frameworks/middleware 954, applications 956 or presentation layer 958. These layers of software architecture executing within the virtual machine 948 can be the same as corresponding layers previously described or may be different.

Certain examples are described herein as including logic or a number of components, modules, or mechanisms.

Modules may constitute either software modules (e.g., code embodied (1) on a non-transitory machine-readable medium or (2) in a transmission signal) or hardware-implemented modules. A hardware-implemented module is a tangible unit capable of performing certain operations and may be configured or arranged in a certain manner. In examples, one or more computer systems (e.g., a standalone, client, or server computer system) or one or more hardware processors may be configured by software (e.g., an application or application portion) as a hardware-implemented module that operates to perform certain operations as described herein.

In various examples, a hardware-implemented module may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or another programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" should be understood to encompass a tangible entity, be that an entity that is physically constructed, permanently configured (e.g., hardwired), or temporarily or transitorily configured (e.g., programmed) to operate in a certain manner or to perform certain operations described herein. Considering examples in which hardware-implemented modules are temporarily configured (e.g., programmed), each of the hardware-implemented modules need not be configured or instantiated at any one instance in time. For example, where the hardware-implemented modules comprise, a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules can provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses that connect the hardware-implemented modules). In examples in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and store the output of that operation in a memory device to which it is communicatively coupled. A further hardware-implemented module may then, at a later time, access the memory device to retrieve and process the stored output. Hardware-implemented modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some examples, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some examples, the processor or processors may be located in a single location (e.g., within a home environment, an office environment, or a server farm), while in other examples the processors may be distributed across a number of locations.

The one or more processors may also operate to support performance of the relevant operations in a "cloud computing" environment or as a "software as a service (SaaS)." For example, at least some of the operations may be performed by a group of computers (as examples of machines including processors), these operations being accessible via a network (e.g., the Internet) and via one or more appropriate interfaces (e.g., APIs).

Examples may be implemented in digital electronic circuitry, or in computer hardware, firmware, or software, or in combinations of them. Examples may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a standalone program or as a module, subroutine, or other unit suitable for use in a computing environment. A computer program can be deployed to be executed on one computer or on multiple computers at one site or distributed across multiple sites and interconnected by a communication network.

In examples, operations may be performed by one or more programmable processors executing a computer program to perform functions by operating on input data and generating output. Method operations can also be performed by, and apparatus of some examples may be implemented as, special purpose logic circuitry, e.g., an FPGA or an ASIC.

The computing system can include clients and servers. A client and server are generally remote from each other and typically interact through a communication network. The relationship of client and server arises by virtue of computer programs running on the respective computers and having a client-server relationship to each other. In examples deploying a programmable computing system, it will be appreciated that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or in a combination of permanently and temporarily configured hardware may be a design choice. Below are set out hardware (e.g., machine) and software architectures that may be deployed, in various examples.

Figure 10:
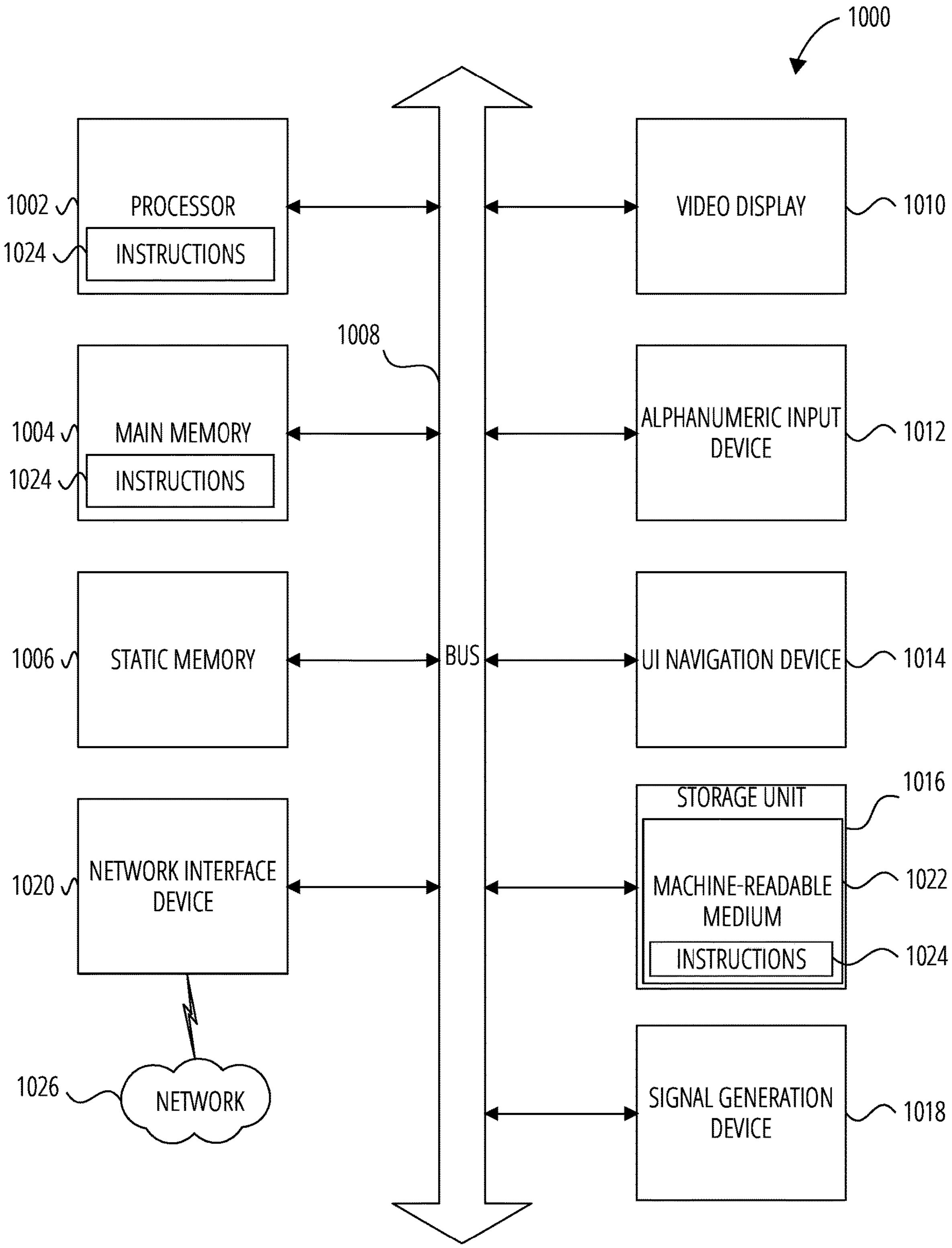
FIG. 10 is a block diagram of a machine in the form of a computer system, according to some examples, within which instructions may be executed for causing the machine to perform any one or more of the methodologies discussed herein.

FIG. 10 is a block diagram of a machine in the example form of a computer system 1000 within which instructions 1024 may be executed for causing the machine to perform any one or more of the methodologies discussed herein. In alternative examples, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a personal digital assistant (PDA), a cellular telephone, a web appliance, a network router, switch, or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1000 includes a processor 1002 (e.g., a central processing unit (CPU), a graphics processing unit (GPU), or both), a main memory 1004, and a static memory 1006, which communicate with each other via a bus 1008. The computer system 1000 may further include a video display unit 1010 (e.g., a liquid crystal display (LCD) or a cathode ray tube (CRT)). The computer system 1000 also includes an alphanumeric input device 1012 (e.g., a keyboard or a touch-sensitive display screen), a user interface navigation (or cursor control) device 1014 (e.g., a mouse), a storage unit 1016, a signal generation device 1018 (e.g., a speaker), and a network interface device 1020.

The storage unit 1016 includes a machine-readable medium 1022 on which is stored one or more sets of data structures and instructions 1024 (e.g., software) embodying or utilized by any one or more of the methodologies or functions described herein. The instructions 1024 may also reside, completely or at least partially, within the main memory 1004 or within the processor 1002 during execution thereof by the computer system 1000, with the main memory 1004 and the processor 1002 also each constituting a machine-readable medium 1022.

While the machine-readable medium 1022 is shown in accordance with some examples to be a single medium, the term "machine-readable medium" may include a single medium or multiple media (e.g., a centralized or distributed database, or associated caches and servers) that store the one or more instructions 1024 or data structures. The term "machine-readable medium" shall also be taken to include any tangible medium that is capable of storing, encoding, or carrying instructions 1024 for execution by the machine and that cause the machine to perform any one or more of the methodologies of the present disclosure, or that is capable of storing, encoding, or carrying data structures utilized by or associated with such instructions 1024. The term "machine-readable medium" shall accordingly be taken to include, but not be limited to, solid-state memories, and optical and magnetic media. Specific examples of a machine-readable medium 1022 include non-volatile memory, including by way of example semiconductor memory devices, e.g., erasable programmable read-only memory (EPROM), electrically erasable programmable read-only memory (EEPROM), and flash memory devices; magnetic disks such as internal hard disks and removable disks; magneto-optical disks; and compact disc read-only memory (CD-ROM) and digital versatile disc read-only memory (DVD-ROM) disks. A machine-readable medium is not a transmission medium.

The instructions 1024 may further be transmitted or received over a communications network 1026 using a transmission medium. The instructions 1024 may be transmitted using the network interface device 1020 and any one of a number of well-known transfer protocols (e.g., hypertext transport protocol (HTTP)). Examples of communication networks include a local area network (LAN), a wide area network (WAN), the Internet, mobile telephone networks, plain old telephone (POTS) networks, and wireless data networks (e.g., Wi-Fi and Wi-Max networks). The term "transmission medium" shall be taken to include any intangible medium that is capable of storing, encoding, or carrying instructions 1024 for execution by the machine, and includes digital or analog communications signals or other intangible media to facilitate communication of such software.

In view of the above-described implementations of subject matter this application discloses the following list of examples, wherein one feature of an example in isolation, or more than one feature of an example taken in combination, and, optionally, in combination with one or more features of one or more further examples, are further examples also falling within the disclosure of this application.

Example 1 is a system comprising: a memory that stores instructions; and one or more processors configured by the instructions to perform operations comprising: causing presentation of a graphical user interface (GUI) at a user device; receiving, via the GUI, first data identifying a plurality of species associated with a geographic region; accessing second data comprising, for each species, a reference value and a current value of each of a plurality of biodiversity metrics; generating, based on the second data, a biodiversity indicator for the geographic region; automatically generating a graphical element that includes, the biodiversity indicator; and causing presentation, via the GUI, of the graphical element at the user device.

In Example 2, the subject matter of Example 1 includes, wherein the biodiversity indicator provides a numerical representation of biodiversity in the geographic region.

In Example 3, the subject matter of Examples 1-2 includes, wherein generating the biodiversity indicator comprises: generating, based on the second data, a reference index value and a current index value for each respective species; aggregating the reference index values to obtain a reference biodiversity index score for the geographic region; aggregating the current index values to obtain a current biodiversity index score for the geographic region; and automatically comparing the current biodiversity index score with the reference biodiversity index score to obtain the biodiversity indicator.

In Example 4, the subject matter of Example 3 includes, wherein generating the reference index value and the current index value for each respective species comprises: generating a reference weighting coefficient for the respective species; applying the reference weighting coefficient to the reference value of at least one of the biodiversity metrics to obtain the reference index value; generating a current weighting coefficient for the respective species; and applying the current weighting coefficient to the current value of at least one of the biodiversity metrics to obtain the current index value.

In Example 5, the subject matter of Examples 3-4 includes, wherein generating the current index value for each respective species comprises: determining whether to apply a penalty to the current index value based on whether a penalty criterion is met for the respective species.

In Example 6, the subject matter of Example 5 includes, wherein the plurality of biodiversity metrics includes an abundance metric, and wherein the penalty criterion is met if the current value of the abundance metric for the respective species exceeds the reference value of the abundance metric for the respective species by a threshold value.

In Example 7, the subject matter of Examples 1-6 includes, the operations further comprising: automatically converting the biodiversity indicator from a non-standardized format to a standardized format for presentation within the GUI.

In Example 8, the subject matter of Example 7 includes, wherein the standardized format comprises an expression of a current biodiversity index score for the geographic region as a percentage of a reference biodiversity index score for the geographic region.

In Example 9, the subject matter of Examples 1-8 includes, wherein the graphical element is a first graphical element, the operations further comprising: automatically generating a second graphical element that includes a reference indicator for the geographic region; and causing presentation of the second graphical element in association with the first graphical element within the GUI, wherein the second graphical element is visually distinguished from the first graphical element.

In Example 10, the subject matter of Examples 1-9 includes, wherein the graphical element is a first graphical element, the operations further comprising: generating, based on the first data, a species richness value for the geographic region; automatically generating a third graphical element that includes the species richness value; and causing presentation of the third graphical element with the first graphical element within the GUI.

In Example 11, the subject matter of Examples 1-10 includes, wherein the graphical element is a first graphical element, and wherein the biodiversity metrics include a bio-dominance metric, the operations further comprising: receiving, via the GUI, third data comprising a size of the geographic region; generating, based on the third data and the current values of the bio-dominance metric, a concentration indicator for the geographic region; automatically generating a fourth graphical element that includes the concentration indicator; and causing presentation of the fourth graphical element with the first graphical element within the GUI.

In Example 12, the subject matter of Examples 1-11 includes, wherein the first data identifies one or more categories of each species, the one or more categories comprising at least one of: fauna, flora, land, air, water, ocean, migratory, or invasive.

In Example 13, the subject matter of Example 12 includes, the operations further comprising: detecting that a particular species of the plurality of species is categorized as invasive with respect to the geographic region; and automatically reducing a value of the biodiversity indicator based on the categorization of the particular species as invasive with respect to the geographic region.

In Example 14, the subject matter of Examples 12-13 includes, the operations further comprising: detecting that a particular species of the plurality of species is categorized as migratory with respect to the geographic region; and automatically applying a reduced weighting coefficient with respect to the particular species based on the categorization of the particular species as migratory with respect to the geographic region.

In Example 15, the subject matter of Examples 1-14 includes, wherein the biodiversity metrics comprise at least one of: an abundance metric, a bio-dominance metric, a scarcity metric, a migration metric, a permanence metric, an overpopulation metric, a species richness metric, or an evenness metric.

In Example 16, the subject matter of Examples 1-15 includes, wherein the reference values represent historic values of the plurality of biodiversity metrics at a determinable date.

In Example 17, the subject matter of Examples 1-16 includes, wherein the memory and the one or more processors form part of a portable computing device.

In Example 18, the subject matter of Examples 1-17 includes, the operations further comprising: providing remote access to the GUI over a network to enable a user to update, via the user device, the current values of the biodiversity metrics, thereby to cause automatic updating of the biodiversity indicator within the GUI.

Example 19 is a method comprising: causing presentation of a graphical user interface (GUI) at a user device; receiving, via the GUI, first data identifying a plurality of species associated with a geographic region; accessing second data comprising, for each species, a reference value and a current value of each of a plurality of biodiversity metrics; generating, based on the second data, a biodiversity indicator for the geographic region; automatically generating a graphical element that includes, the biodiversity indicator; and causing presentation, via the GUI, of the graphical element at the user device.

Example 20 is a non-transitory computer-readable medium that stores instructions that, when executed by one or more processors, cause the one or more processors to perform operations comprising: causing presentation of a graphical user interface (GUI) at a user device; receiving, via the GUI, first data identifying a plurality of species associated with a geographic region; accessing second data comprising, for each species, a reference value and a current value of each of a plurality of biodiversity metrics; generating, based on the second data, a biodiversity indicator for the geographic region; automatically generating a graphical element that includes, the biodiversity indicator; and causing presentation, via the GUI, of the graphical element at the user device.

Example 21 is at least one machine-readable medium including instructions that, when executed by processing circuitry, cause the processing circuitry to perform operations to implement any of Examples 1-20.

Example 22 is an apparatus comprising means to implement any of Examples 1-20.

Example 23 is a system to implement any of Examples 1-20.

Example 24 is a method to implement any of Examples 1-20.

Examples of the present disclosure thus provide a technological tool suitable for generating biodiversity indicators, or biodiversity index values. A multifaceted approach may provide a comprehensive and highly automated assessment of ecosystem health, species diversity and ecological balance. By combining various factors, such as (for example) abundance, bio-dominance, scarcity, species richness, and biomass per hectare, the tool described herein may provide a versatile and robust system facilitating assessment or protection of biodiversity.

Bio-dominance may be employed to take the relative influence of a species on an ecosystem into account, while species richness identifies a total number of different species in the ecosystem. A scarcity factor may, for example, be derived from an official CITES or IUCN indicator, and may also consider other aspects, such as a gene pool threat formula.

The tool may also automatically analyze and respond to invasive species being included in a geographic region, and adjust output based on migration patterns. This may apply to various durations and types of migrations, including land, air, seawater, freshwater, or specialized migrations. For example, the tool may include subcategories identifying migrations, such as amphibian migrations from freshwater to land, and migrations between sea water and freshwater, such as salmon, having an effect on different areas as they migrate.

Additional factors may be applied in generating, for example, the current biodiversity index score for a particular region. In some examples, a "consistency value" may be applied to adjust a biodiversity index score. Consistency values may vary from region to region, and may be determined based on risk factors associated with the region. For example, a consistency value may provide an indication of the degree of risk in maintaining the status quo with respect to biodiversity in a specified region. Similar to the concept of an interest rate, at certain times a consistency value for a specific region may be higher than at other times. For instance, the extent to which climate change impacts on a specific region may cause its consistency value to change over time, e.g., a higher consistency value may denote higher climate change risks, resulting in downward adjustment of current biodiversity index scores. Referring back to the example of "biodiversity credits" above, the "interest" in this context may be capitalized into the price of biodiversity credits issued with respect to a specific biodiversity indicator and geographic region.

While examples disclosed herein focus on identification and scoring of biodiversity in organisms on a per-species level, it will be appreciated that similar techniques may be applied on other levels without departing from the scope of the disclosure. For example, species may be grouped according to certain predefined characteristics and scoring may be performed on a per-group level. A user may also be able to define a "species," thus not limiting the use of the tool to specific, pre-defined species listings.

Although specific examples are described herein, it will be evident that various modifications and changes may be made to these examples without departing from the broader spirit and scope of the disclosure. Accordingly, the specification and drawings are to be regarded in an illustrative rather than a restrictive sense. The accompanying drawings that form a part hereof show by way of illustration, and not of limitation, specific examples in which the subject matter may be practiced. The examples illustrated are described in sufficient detail to enable those skilled in the art to practice the teachings disclosed herein. Other examples may be utilized and derived therefrom, such that structural and logical substitutions and changes may be made without departing from the scope of this disclosure. This detailed description, therefore, is not to be taken in a limiting sense, and the scope of various examples is defined only by the appended claims, along with the full range of equivalents to which such claims are entitled.

Such examples of the inventive subject matter may be referred to herein, individually or collectively, by the "example" merely for convenience and without intending to voluntarily limit the scope of this application to any single example or concept if more than one is in fact disclosed. Thus, although specific examples have been illustrated and described herein, it should be appreciated that any arrangement calculated to achieve the same purpose may be substituted for the specific examples shown. This disclosure is intended to cover any and all adaptations or variations of various examples. Combinations of the above examples, and other examples not specifically described herein, will be apparent to those of skill in the art upon reviewing the above description.

The various features, steps, operations, and processes described herein may be used independently of one another, or may be combined in various ways. All possible combinations and subcombinations are intended to fall within the scope of this disclosure. In addition, certain method or process blocks or operations may be omitted in some implementations.

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" and "an" are herein used, as is common in patent documents, to include one or more than one instance. Finally, as used herein, the conjunction "or" refers to a non-exclusive "or," unless specifically stated otherwise.

Unless the context clearly requires otherwise, throughout the description and the claims, the words "comprise," "comprising," and the like are to be construed in an inclusive sense, as opposed to an exclusive or exhaustive sense, e.g., in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words using the singular or plural number may also include the plural or singular number, respectively. The word "or" in reference to a list of two or more items, covers all of the following interpretations of the word: any one of the items in the list, all of the items in the list, and any combination of the items in the list.

As used in this disclosure, phrases of the form "at least one of an A, a B, or a C," "at least one of A, B, or C," "at least one of A, B, and C," and the like, should be interpreted to select at least one from the group that comprises "A, B, and C." Unless explicitly stated otherwise in connection with a particular instance in this disclosure, this manner of phrasing does not mean "at least one of A, at least one of B, and at least one of C." As used in this disclosure, the example "at least one of an A, a B, or a C," would cover any of the following selections: {A}, {B}, {C}, {A, B}, {A, C}, {B, C}, and {A, B, C}.

Although some examples, e.g., those depicted in the drawings, include a particular sequence of operations, the sequence may be altered without departing from the scope of the present disclosure. For example, some of the operations depicted may be performed in parallel or in a different sequence that does not materially affect the functions as described in the examples. In other examples, different components of an example device or system that implements an example method may perform functions at substantially the same time or in a specific sequence.

What is claimed is:

1. A system comprising:

a memory that stores instructions; and one or more processors configured by the instructions to perform operations comprising:

causing presentation of a graphical user interface (GUI) at a user device;

receiving, via the GUI, first data identifying a plurality of species associated with a geographic region;

accessing second data comprising, for each species, a reference value and a current value of each of a plurality of biodiversity metrics;

generating, based on the second data, a biodiversity indicator for the geographic region;

automatically generating a graphical element that includes the biodiversity indicator; and causing presentation, via the GUI, of the graphical element at the user device.

2. The system of claim 1, wherein the biodiversity indicator provides a numerical representation of biodiversity in the geographic region.

3. The system of claim 1, wherein generating the biodiversity indicator comprises:

generating, based on the second data, a reference index value and a current index value for each respective species;

aggregating the reference index values to obtain a reference biodiversity index score for the geographic region;

aggregating the current index values to obtain a current biodiversity index score for the geographic region; and automatically comparing the current biodiversity index score with the reference biodiversity index score to obtain the biodiversity indicator.

4. The system of claim 3, wherein generating the reference index value and the current index value for each respective species comprises:

generating a reference weighting coefficient for the respective species;

applying the reference weighting coefficient to the reference value of at least one of the biodiversity metrics to obtain the reference index value;

generating a current weighting coefficient for the respective species; and applying the current weighting coefficient to the current value of at least one of the biodiversity metrics to obtain the current index value.

5. The system of claim 3, wherein generating the current index value for each respective species comprises:

determining whether to apply a penalty to the current index value based on whether a penalty criterion is met for the respective species.

6. The system of claim 5, wherein the plurality of biodiversity metrics includes an abundance metric, and wherein the penalty criterion is met if the current value of the abundance metric for the respective species exceeds the reference value of the abundance metric for the respective species by a threshold value.

7. The system of claim 1, the operations further comprising:

automatically converting the biodiversity indicator from a non-standardized format to a standardized format for presentation within the GUI.

8. The system of claim 7, wherein the standardized format comprises an expression of a current biodiversity index score for the geographic region as a percentage of a reference biodiversity index score for the geographic region.

9. The system of claim 1, wherein the graphical element is a first graphical element, the operations further comprising:

automatically generating a second graphical element that includes a reference indicator for the geographic region; and causing presentation of the second graphical element in association with the first graphical element within the GUI, wherein the second graphical element is visually distinguished from the first graphical element.

10. The system of claim 1, wherein the graphical element is a first graphical element, the operations further comprising:

generating, based on the first data, a species richness value for the geographic region;

automatically generating a third graphical element that includes the species richness value; and causing presentation of the third graphical element with the first graphical element within the GUI.

11. The system of claim 1, wherein the graphical element is a first graphical element, and wherein the biodiversity metrics include a bio-dominance metric, the operations further comprising:

receiving, via the GUI, third data comprising a size of the geographic region;

generating, based on the third data and the current values of the bio-dominance metric, a concentration indicator for the geographic region;

automatically generating a fourth graphical element that includes the concentration indicator; and causing presentation of the fourth graphical element with the first graphical element within the GUI.

12. The system of claim 1, wherein the first data identifies one or more categories of each species, the one or more categories comprising at least one of: fauna, flora, land, air, water, ocean, migratory, or invasive.

13. The system of claim 12, the operations further comprising:

detecting that a particular species of the plurality of species is categorized as invasive with respect to the geographic region; and automatically reducing a value of the biodiversity indicator based on the categorization of the particular species as invasive with respect to the geographic region.

14. The system of claim 12, the operations further comprising:

detecting that a particular species of the plurality of species is categorized as migratory with respect to the geographic region; and automatically applying a reduced weighting coefficient with respect to the particular species based on the categorization of the particular species as migratory with respect to the geographic region.

15. The system of claim 1, wherein the biodiversity metrics comprise at least one of: an abundance metric, a bio-dominance metric, a scarcity metric, a migration metric, a permanence metric, an overpopulation metric, a species richness metric, or an evenness metric.

16. The system of claim 1, wherein the reference values represent historic values of the plurality of biodiversity metrics at a determinable date.

17. The system of claim 1, wherein the memory and the one or more processors form part of a portable computing device.

18. The system of claim 1, the operations further comprising:

providing remote access to the GUI over a network to enable a user to update, via the user device, the current values of the biodiversity metrics, thereby to cause automatic updating of the biodiversity indicator within the GUI.

19. A method comprising:

causing presentation of a graphical user interface (GUI) at a user device;

receiving, via the GUI, first data identifying a plurality of species associated with a geographic region;

accessing second data comprising, for each species, a reference value and a current value of each of a plurality of biodiversity metrics;

generating, based on the second data, a biodiversity indicator for the geographic region;

automatically generating a graphical element that includes the biodiversity indicator; and causing presentation, via the GUI, of the graphical element at the user device.

20. A non-transitory computer-readable medium that stores instructions that, when executed by one or more processors, cause the one or more processors to perform operations comprising:

causing presentation of a graphical user interface (GUI) at a user device;

receiving, via the GUI, first data identifying a plurality of species associated with a geographic region;

accessing second data comprising, for each species, a reference value and a current value of each of a plurality of biodiversity metrics;

generating, based on the second data, a biodiversity indicator for the geographic region;

automatically generating a graphical element that includes the biodiversity indicator; and causing presentation, via the GUI, of the graphical element at the user device.

* * * * *